(12) United States Patent
Silvestro

(10) Patent No.: US 9,301,777 B2
(45) Date of Patent: Apr. 5, 2016

(54) OCCLUSION BYPASSING APPARATUSES AND METHODS FOR BYPASSING AN OCCLUSION IN A BLOOD VESSEL

(71) Applicant: Invatec, S.p.A., Roncadelle (BS) (IT)

(72) Inventor: Claudio Silvestro, Roncadelle (IT)

(73) Assignee: Invatec S.p.A., Roncadelle (IT)

( * ) Notice: Subject to any disclaimer, the term of this patent is extended or adjusted under 35 U.S.C. 154(b) by 213 days.

(21) Appl. No.: 13/952,973

(22) Filed: Jul. 29, 2013

(65) Prior Publication Data

US 2015/0032141 A1 Jan. 29, 2015

(51) Int. Cl.
| | |
|---|---|
| *A61B 17/34* | (2006.01) |
| *A61M 25/01* | (2006.01) |
| *A61M 25/00* | (2006.01) |
| *A61B 17/22* | (2006.01) |
| *A61B 17/00* | (2006.01) |

(52) U.S. Cl.
CPC ........ *A61B 17/3478* (2013.01); *A61M 25/0194* (2013.01); *A61B 17/3468* (2013.01); *A61B 2017/00331* (2013.01); *A61B 2017/22095* (2013.01); *A61M 25/0041* (2013.01); *A61M 2025/0197* (2013.01)

(58) Field of Classification Search
CPC ........... A61B 2017/22094; A61B 2017/00252; A61B 2017/22044; A61B 2017/22095; A61M 2025/0197; A61M 25/0194
USPC ......................................................... 606/159
See application file for complete search history.

(56) References Cited

U.S. PATENT DOCUMENTS

| | | | |
|---|---|---|---|
| 4,552,554 A | 11/1985 | Gould et al. |
| 4,774,949 A | 10/1988 | Fogarty |
| 5,707,389 A | 1/1998 | Louw et al. |
| 5,830,222 A | 11/1998 | Makower |
| 5,916,194 A | 6/1999 | Jacobsen et al. |
| 5,947,994 A | 9/1999 | Louw et al. |
| 6,068,638 A | 5/2000 | Makower |
| 6,071,292 A | 6/2000 | Makower et al. |
| 6,081,738 A | 6/2000 | Hinohara et al. |

(Continued)

FOREIGN PATENT DOCUMENTS

| | | |
|---|---|---|
| WO | WO2006/105244 | 10/2006 |
| WO | WO2013/003757 | 1/2013 |

(Continued)

OTHER PUBLICATIONS

PCT/US2014/044170, International Search Report and The Written Opinion, mailed Nov. 11, 2014.

(Continued)

*Primary Examiner* — Katherine M Shi

(57) ABSTRACT

Occlusion bypassing apparatuses are disclosed for re-entering the true lumen of a vessel after subintimally bypassing an occlusion in a vessel. The occlusion bypassing apparatuses include a shaft component and a needle component slidably disposed within the shaft component and having an angled configuration when deployed. In embodiments hereof, the needle component has an angled distal tip segment that may be utilized to selectively bend a flexible distal portion of the shaft component in order to extend the flexible distal portion towards the true lumen of the vessel. The needle component is distally advanced relative to the shaft component to pierce through the intima of the vessel and thereafter enter the true lumen.

20 Claims, 25 Drawing Sheets

(56) References Cited

U.S. PATENT DOCUMENTS

| | | | |
|---|---|---|---|
| 6,159,225 A | 12/2000 | Makower | |
| 6,178,968 B1 | 1/2001 | Louw et al. | |
| 6,190,353 B1 | 2/2001 | Makower et al. | |
| 6,203,524 B1 | 3/2001 | Burney et al. | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,231,563 B1 | 5/2001 | White et al. | |
| 6,231,587 B1 | 5/2001 | Makower et al. | |
| 6,235,000 B1 | 5/2001 | Milo et al. | |
| 6,283,983 B1 | 9/2001 | Makower et al. | |
| 6,287,317 B1 | 9/2001 | Makower et al. | |
| 6,302,875 B1 | 10/2001 | Makower et al. | |
| 6,375,615 B1 | 4/2002 | Makower et al. | |
| 6,379,319 B1 | 4/2002 | Garibotto et al. | |
| 6,432,127 B1 | 8/2002 | Kim et al. | |
| 6,447,477 B2 | 9/2002 | Burney et al. | |
| 6,458,098 B1 | 10/2002 | Kanesaka | |
| 6,508,824 B1 | 1/2003 | Flaherty et al. | |
| 6,511,458 B2 | 1/2003 | Milo et al. | |
| 6,514,217 B1 | 2/2003 | Selmon et al. | |
| 6,544,230 B1 | 4/2003 | Flaherty et al. | |
| 6,579,311 B1 | 6/2003 | Makower | |
| 6,602,241 B2 | 8/2003 | Makower et al. | |
| 6,655,386 B1 | 12/2003 | Makower et al. | |
| 6,669,709 B1 | 12/2003 | Cohn et al. | |
| 6,719,725 B2 | 4/2004 | Milo et al. | |
| 6,726,677 B1 | 4/2004 | Makower et al. | |
| 6,746,464 B1 | 6/2004 | Makower et al. | |
| 7,004,173 B2 | 2/2006 | Sparks et al. | |
| 7,059,330 B1 | 6/2006 | Makower et al. | |
| 7,066,914 B2 | 6/2006 | Andersen | |
| 7,141,041 B2 | 11/2006 | Seward | |
| 7,179,270 B2 | 2/2007 | Makower et al. | |
| 7,316,655 B2 | 1/2008 | Garibotto et al. | |
| 7,357,794 B2 | 4/2008 | Makover et al. | |
| 7,534,223 B2 | 5/2009 | Boutilette et al. | |
| 7,606,615 B2 | 10/2009 | Makower et al. | |
| 7,637,870 B2 | 12/2009 | Flaherty et al. | |
| 7,729,738 B2 | 6/2010 | Flaherty et al. | |
| 7,833,197 B2 | 11/2010 | Boutilette et al. | |
| 7,854,727 B2 | 12/2010 | Belsley | |
| RE42,049 E | 1/2011 | Schroeder et al. | |
| 7,938,819 B2 | 5/2011 | Kugler et al. | |
| 8,083,727 B2 | 12/2011 | Kugler et al. | |
| 8,172,863 B2 | 5/2012 | Robinson et al. | |
| 8,202,246 B2 | 6/2012 | Kugler et al. | |
| 8,221,357 B2 | 7/2012 | Boutillette | |
| 8,226,566 B2 | 7/2012 | Nita | |
| 8,241,311 B2 | 8/2012 | Ward et al. | |
| 8,257,382 B2 | 9/2012 | Rottenberg et al. | |
| 8,323,261 B2 | 12/2012 | Kugler et al. | |
| 8,337,425 B2 | 12/2012 | Olson et al. | |
| 8,388,876 B2 | 3/2013 | Boutilette et al. | |
| 8,460,254 B2 | 6/2013 | Belsley | |
| 8,486,022 B2 | 7/2013 | Ludwig et al. | |
| 8,496,679 B2 | 7/2013 | Robinson et al. | |
| 8,512,310 B2 | 8/2013 | Kugler et al. | |
| 8,535,245 B2 | 9/2013 | Jen et al. | |
| 8,556,857 B2 | 10/2013 | Boutillette | |
| 2001/0000041 A1 | 3/2001 | Selmon et al. | |
| 2002/0072706 A1 | 6/2002 | Hiblar et al. | |
| 2004/0167554 A1 | 8/2004 | Simpson et al. | |
| 2005/0021003 A1 | 1/2005 | Caso et al. | |
| 2005/0171478 A1 | 8/2005 | Selmon et al. | |
| 2006/0094930 A1 | 5/2006 | Sparks et al. | |
| 2006/0276749 A1* | 12/2006 | Selmon et al. | 604/164.01 |
| 2007/0123925 A1 | 5/2007 | Benjamin et al. | |
| 2008/0125748 A1 | 5/2008 | Patel | |
| 2008/0140101 A1* | 6/2008 | Carley et al. | 606/159 |
| 2009/0124899 A1 | 5/2009 | Jacobs et al. | |
| 2009/0209910 A1* | 8/2009 | Kugler et al. | 604/103.1 |
| 2010/0063534 A1 | 3/2010 | Kugler et al. | |
| 2011/0144677 A1 | 6/2011 | Ward et al. | |
| 2011/0264125 A1* | 10/2011 | Wilson et al. | 606/159 |
| 2011/0276079 A1 | 11/2011 | Kugler et al. | |
| 2012/0095485 A1 | 4/2012 | Cully et al. | |
| 2012/0283571 A1 | 11/2012 | Nita | |
| 2012/0283761 A1 | 11/2012 | Rosenthal et al. | |
| 2012/0323251 A1 | 12/2012 | Kugler et al. | |
| 2012/0323269 A1 | 12/2012 | Rottenberg et al. | |
| 2013/0006167 A1 | 1/2013 | Alvarez | |
| 2013/0006173 A1* | 1/2013 | Alvarez et al. | 604/95.05 |
| 2013/0006282 A1 | 1/2013 | Wilkinson | |
| 2013/0072957 A1 | 3/2013 | Anderson | |
| 2013/0103070 A1 | 4/2013 | Kugler et al. | |
| 2013/0116622 A1 | 5/2013 | Takagi | |
| 2013/0158519 A1 | 6/2013 | Boutilette et al. | |
| 2013/0245430 A1 | 9/2013 | Selmon et al. | |
| 2013/0296907 A1 | 11/2013 | Robinson et al. | |
| 2013/0304108 A1 | 11/2013 | Weber et al. | |
| 2013/0310868 A1 | 11/2013 | Kugler et al. | |
| 2013/0317528 A1 | 11/2013 | Anderson et al. | |

FOREIGN PATENT DOCUMENTS

| | | |
|---|---|---|
| WO | WO2013/164825 | 11/2013 |
| WO | WO2014/039096 | 3/2014 |

OTHER PUBLICATIONS

Karkos et al. "Subintimal Recanalization of the Femoropopliteal Segment to Promote Healing of an Ulcerated Below-Knee Amputation Stump" J Endovasc Ther 2006;13:420-423.

Glasby et al. "Subintimal Angioplasty" Review, pp. 12-16, 2008.

Bolia A. "Subintimal Angioplasty, Tips and Technique: How Long Can You Go?"

* cited by examiner

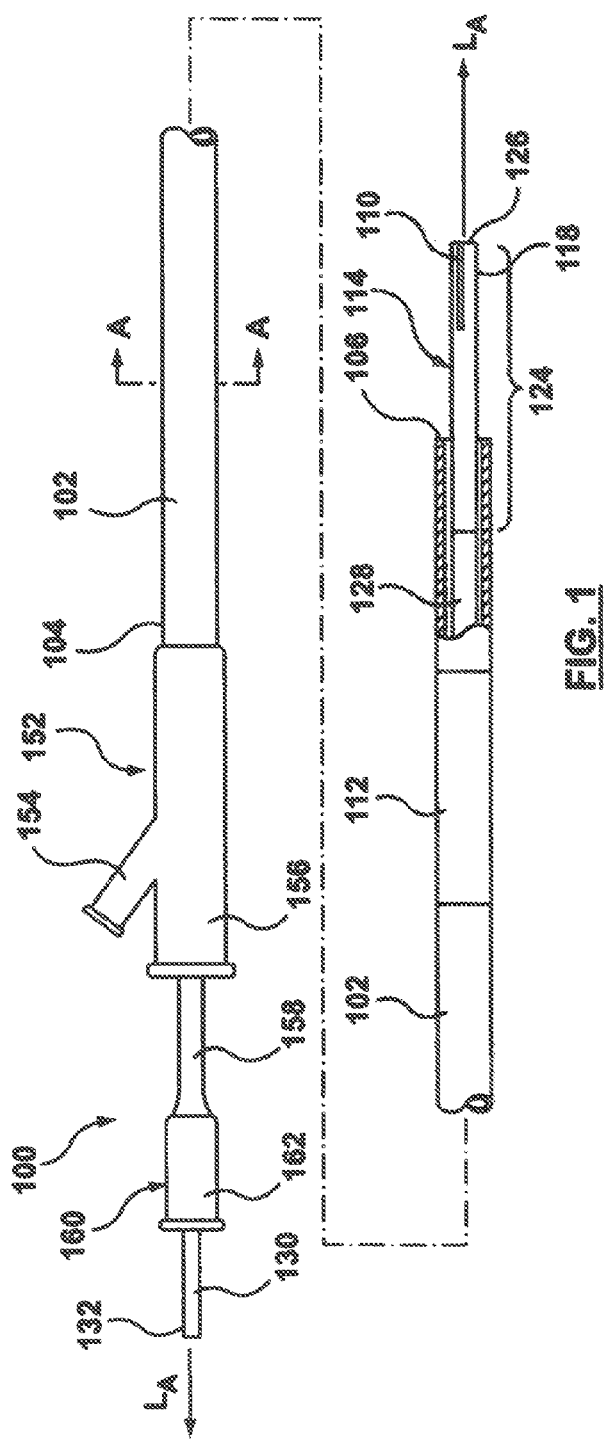
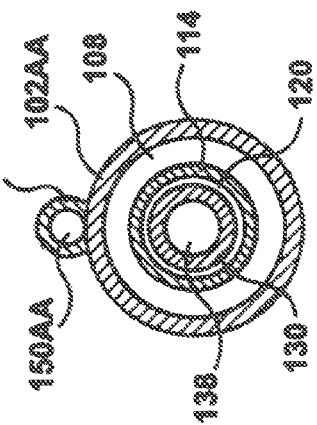
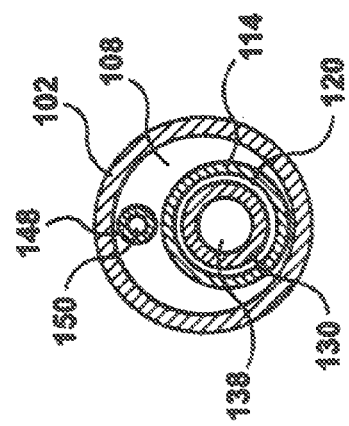

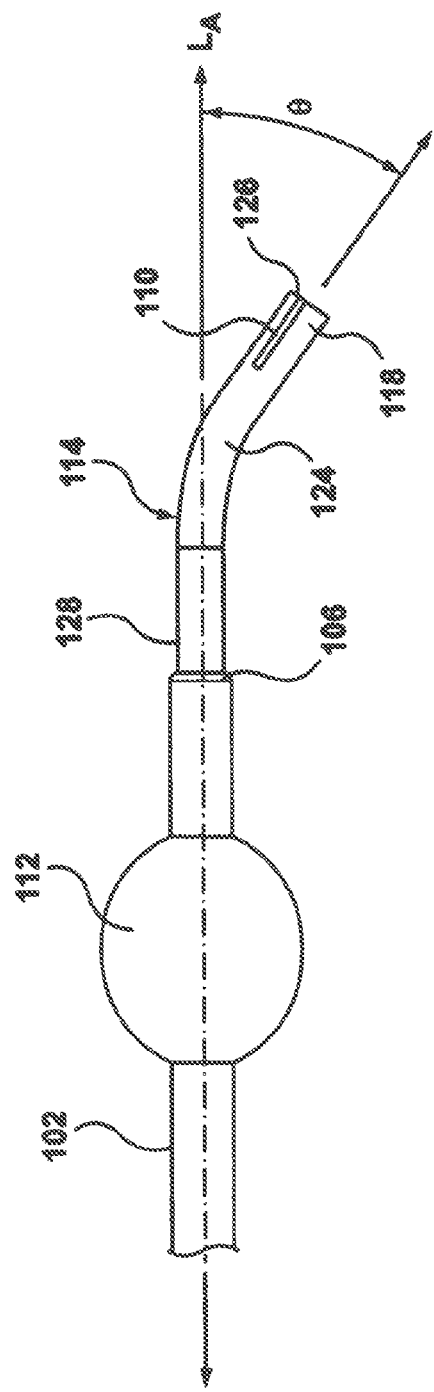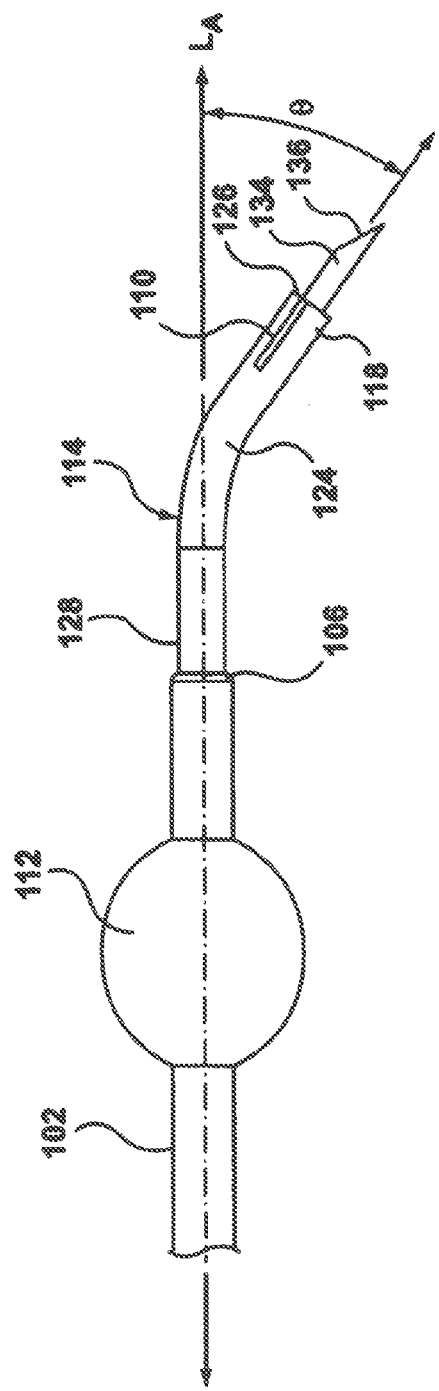

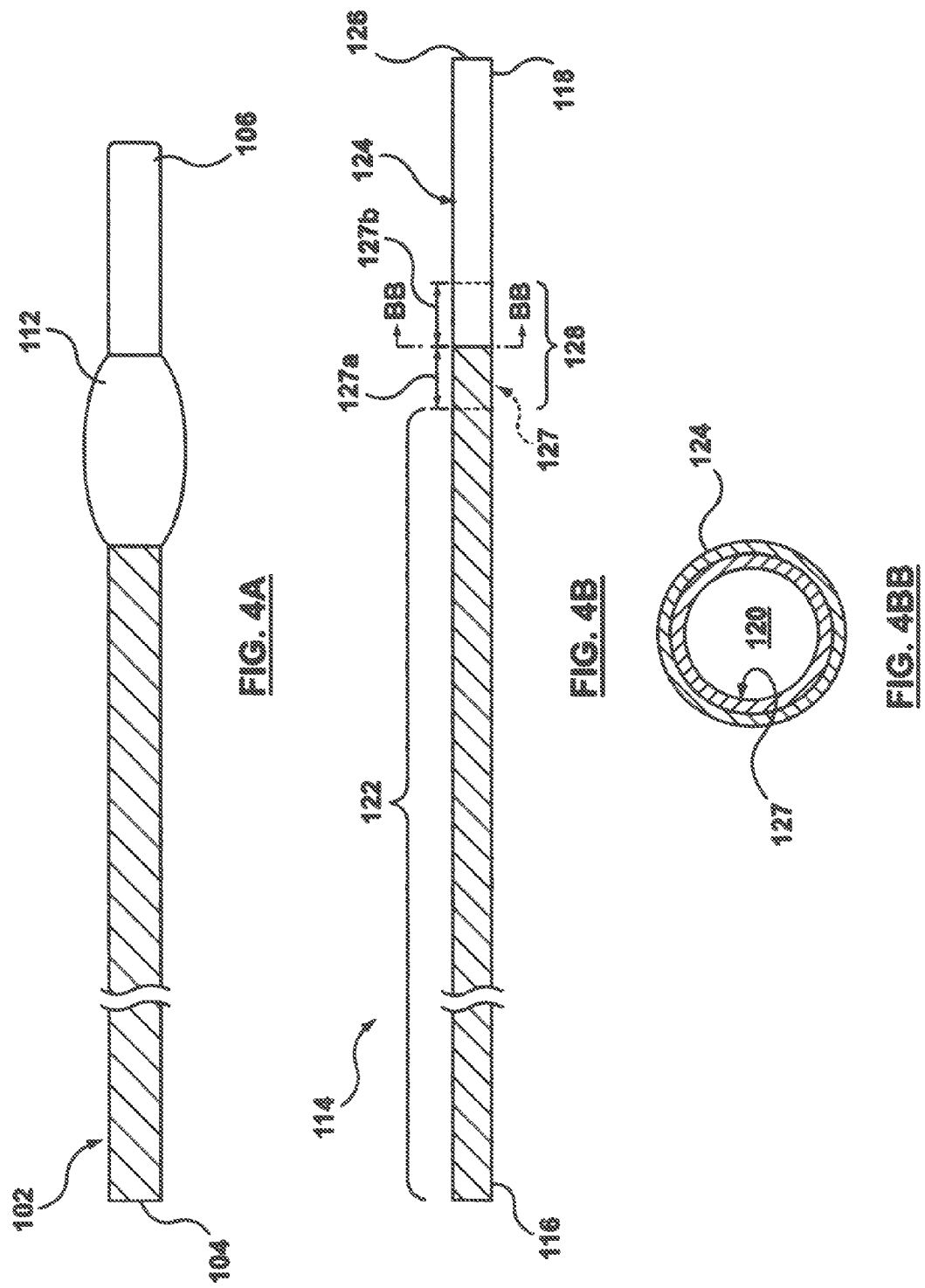

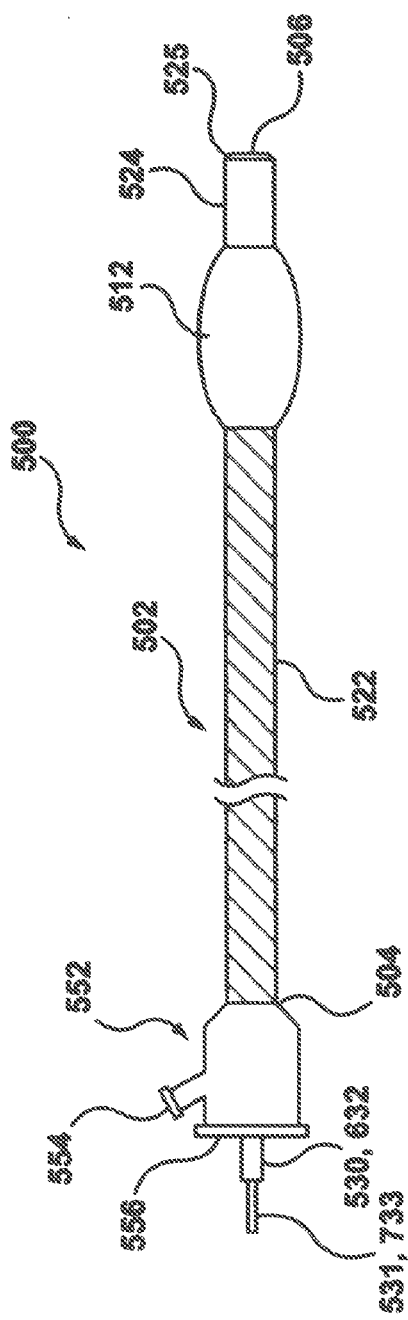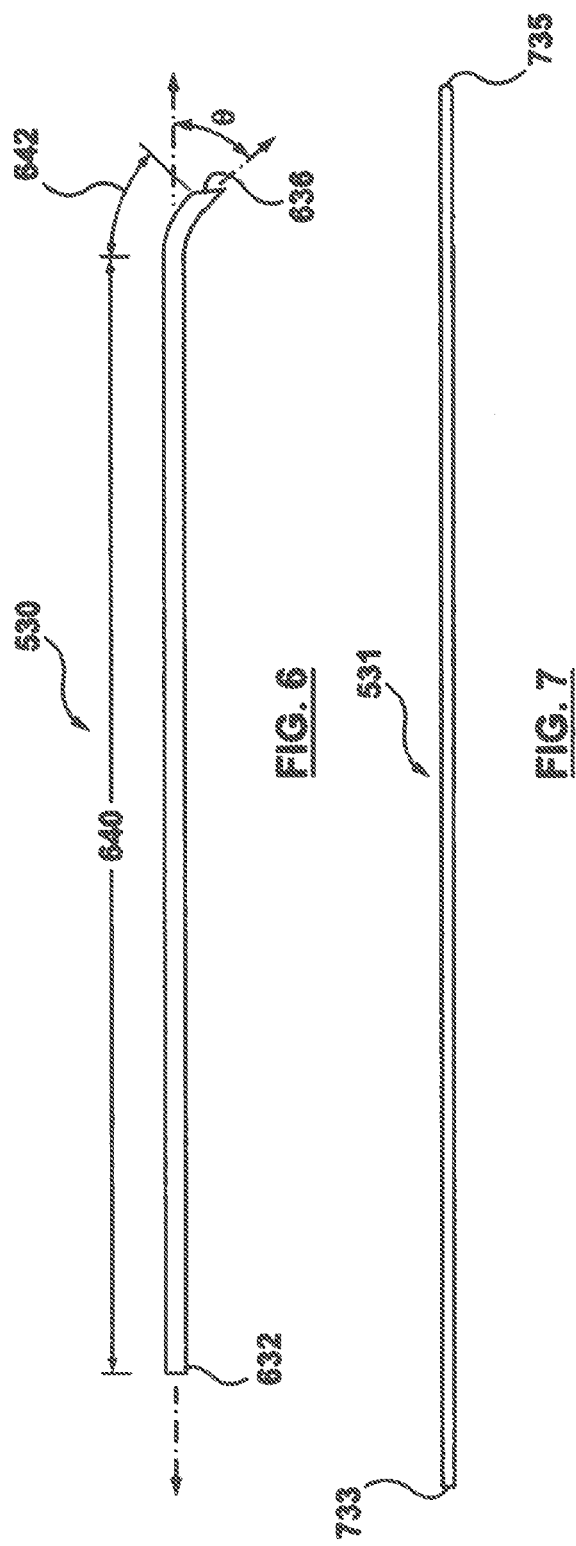

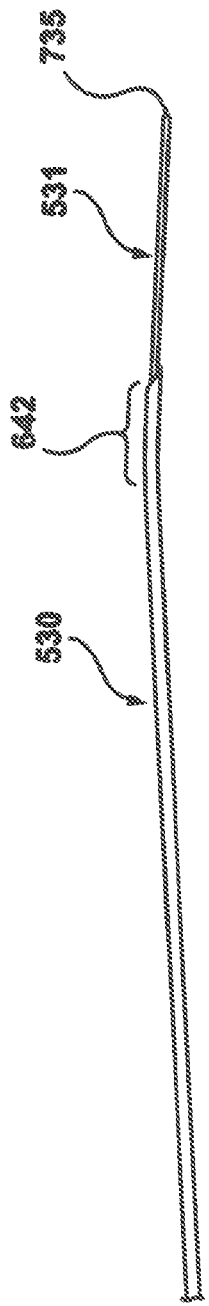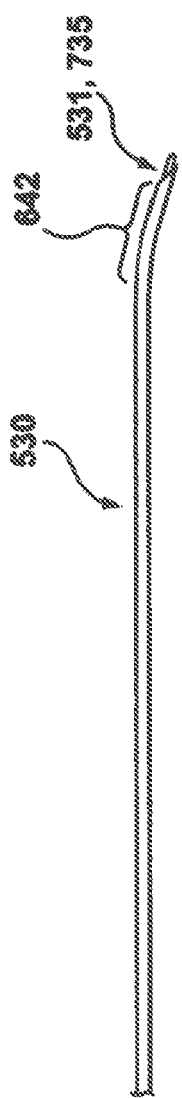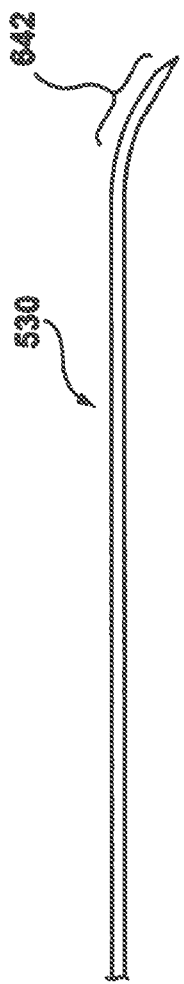

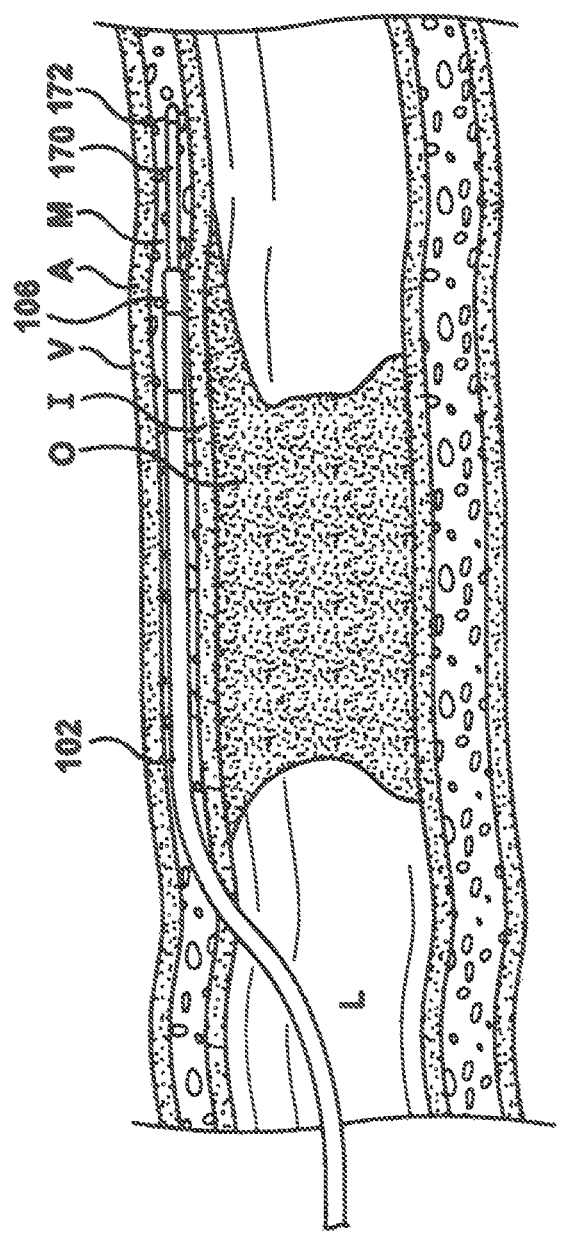

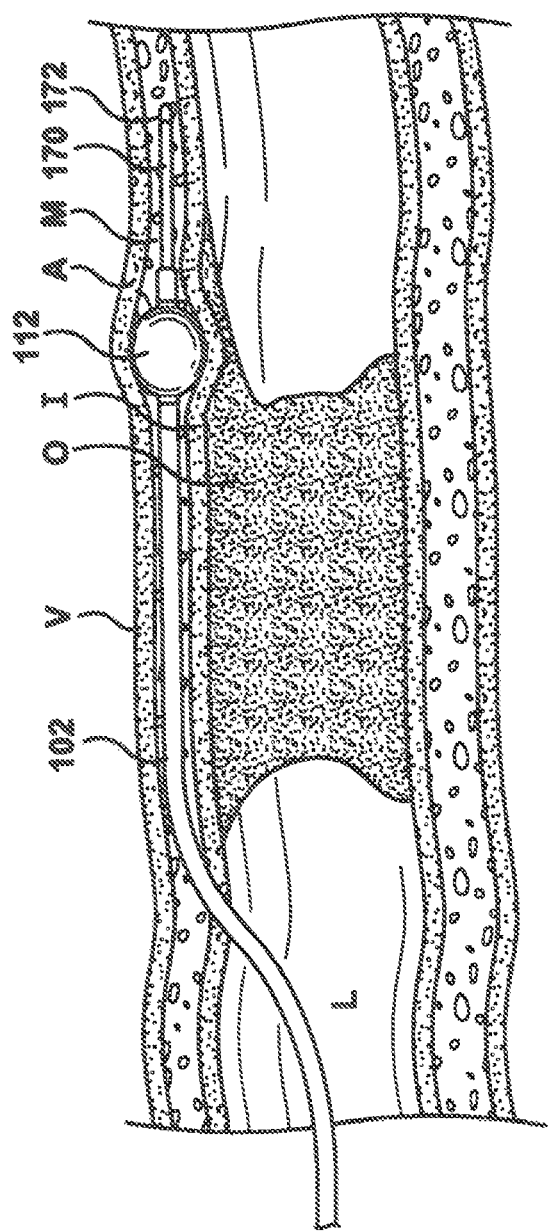

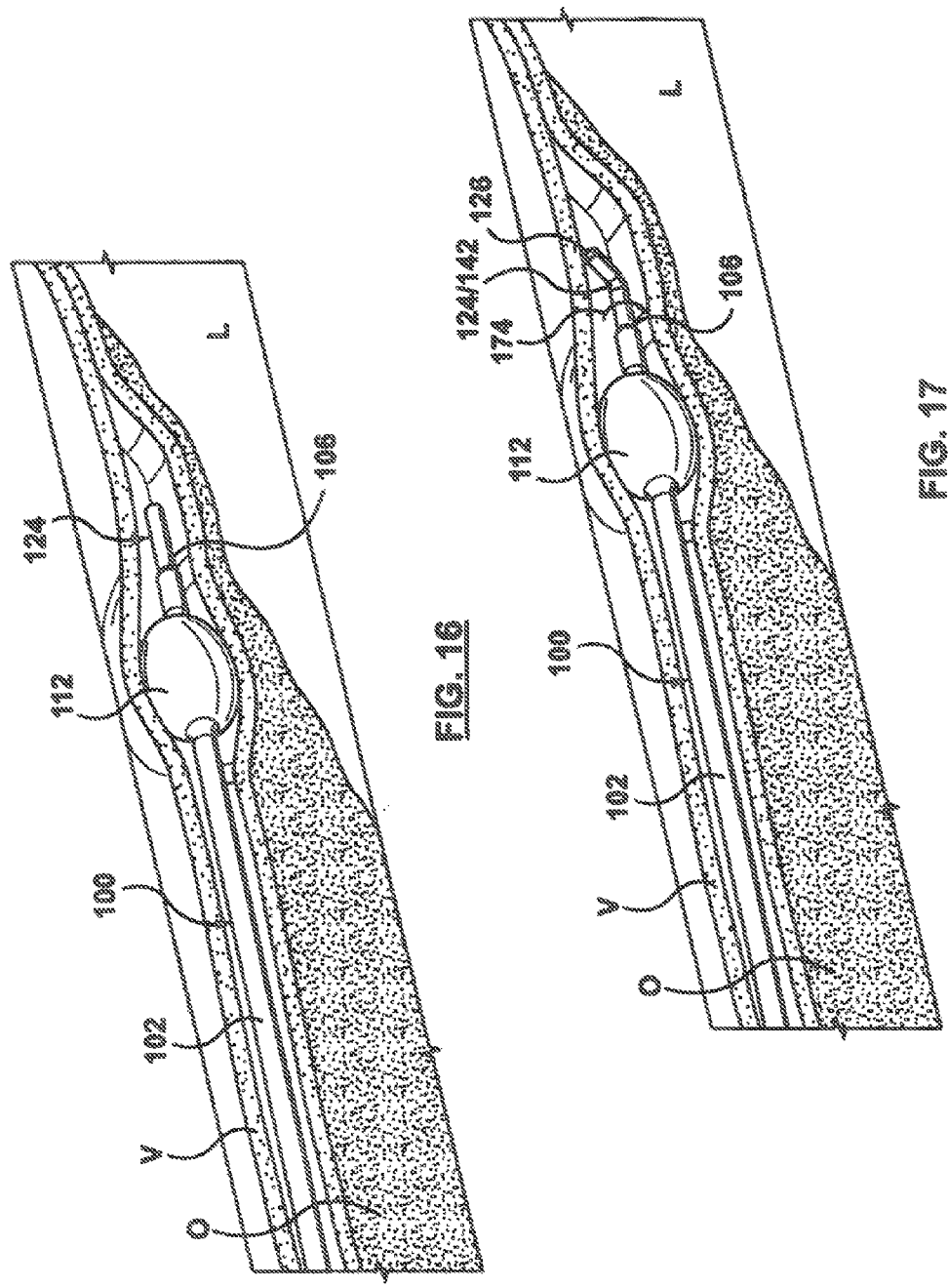

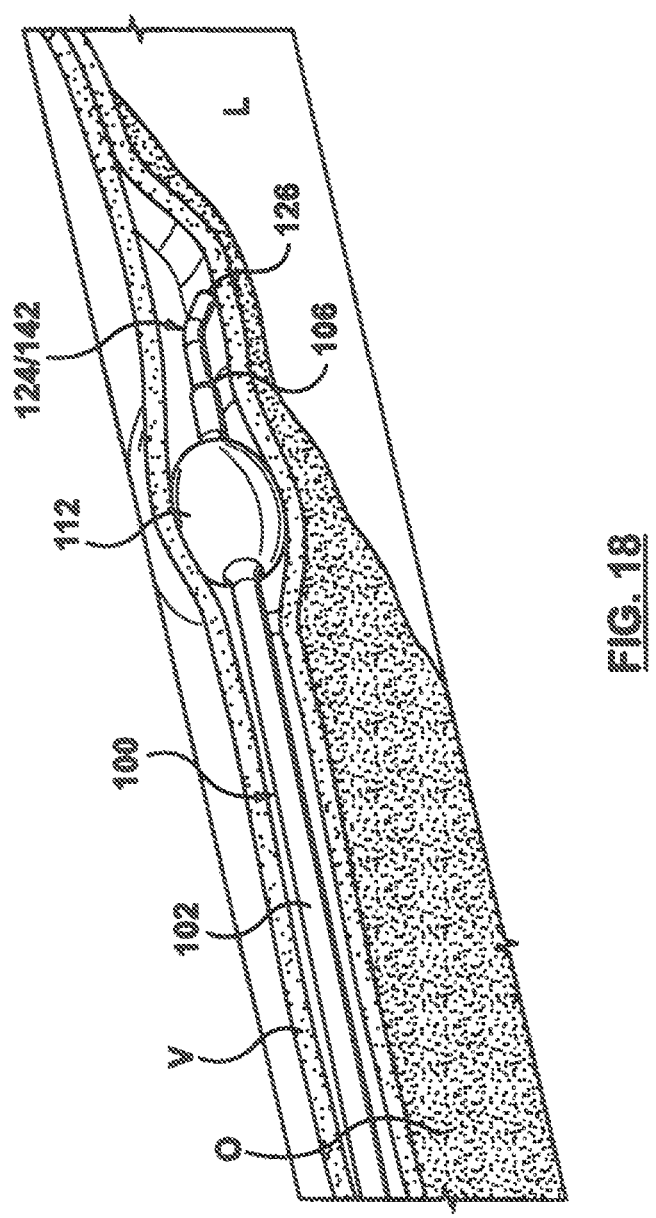

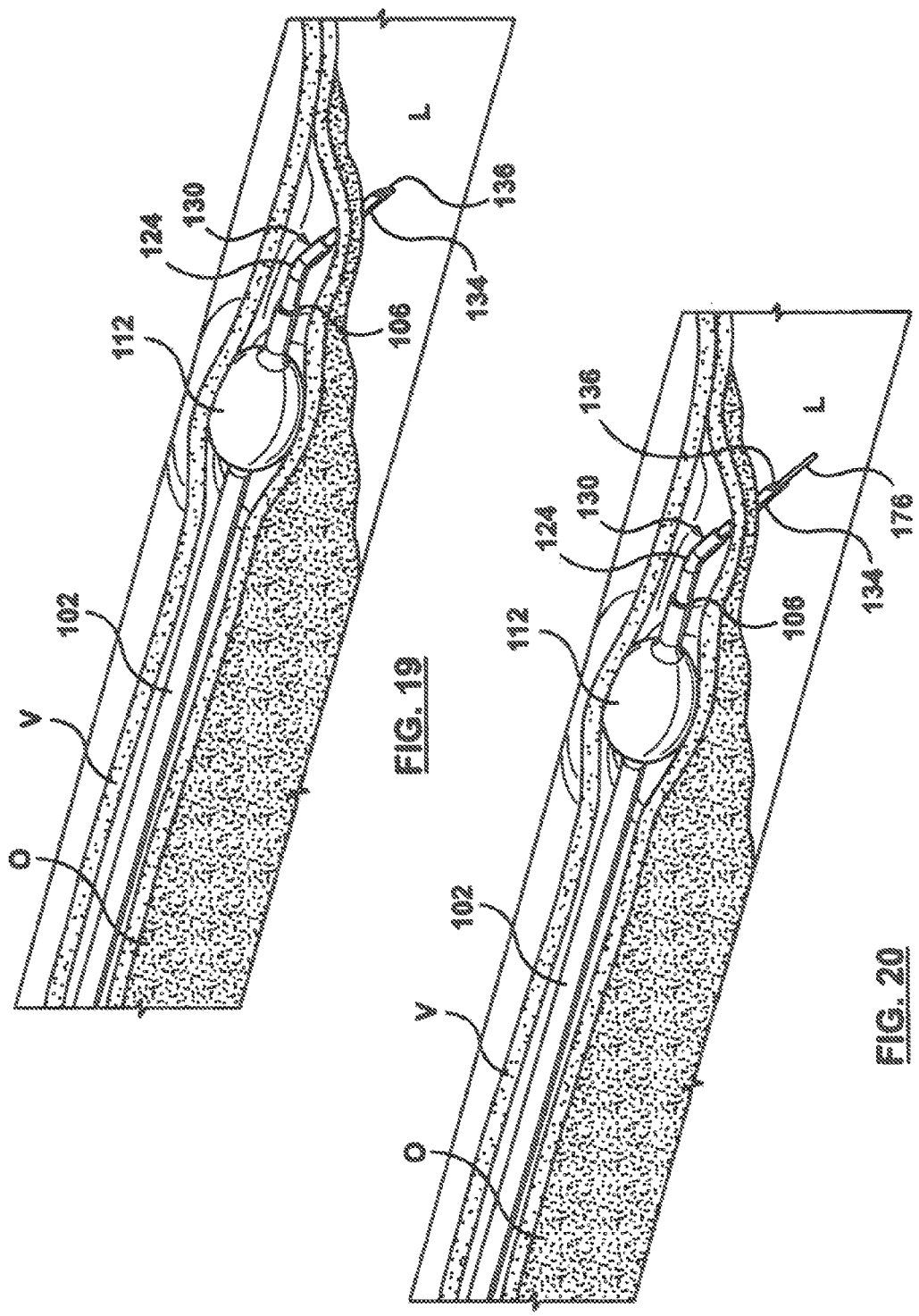

OCCLUSION BYPASSING APPARATUSES AND METHODS FOR BYPASSING AN OCCLUSION IN A BLOOD VESSEL

FIELD OF THE INVENTION

The invention relates generally to occlusion bypassing apparatuses and methods of using such apparatus for subintimally bypassing a blockage in a blood vessel, such as a chronic total occlusion, and reentering the true lumen of the blood vessel distal of the blockage.

BACKGROUND OF THE INVENTION

Cardiovascular disease, including atherosclerosis, is the leading cause of death in the United States. One method for treating atherosclerosis and other forms of arterial lumen narrowing is percutaneous transluminal angioplasty, commonly referred to as "angioplasty" or "PTA," or "PTCA" when performed in the coronary arteries. The objective in angioplasty is to restore adequate blood flow through the affected artery, which may be accomplished by inflating a balloon of a balloon catheter within the narrowed lumen of the artery to dilate the vessel.

The anatomy of arteries varies widely from patient to patient. Often patient's arteries are irregularly shaped, highly tortuous and very narrow. The tortuous configuration of the arteries may present difficulties to a clinician in advancement of the balloon catheter to a treatment site. In addition, in some instances, the extent to which the lumen is narrowed at the treatment site is so severe that the lumen is completely or nearly completely obstructed, which may be described as a total occlusion. Total or near-total occlusions in arteries can prevent all or nearly all of the blood flow through the affected arteries. If the total or near total occlusion has been established for a long period of time, the lesion may be referred to as a chronic total occlusion or CTO. Chronic total occlusions can occur in coronary as well as peripheral arteries. Chronic total occlusions are often characterized by extensive plaque formation and typically include a fibrous cap surrounding softer plaque material. This fibrous cap may present a surface that is difficult to penetrate with a conventional medical guidewire.

A number of devices have been developed and/or used for the percutaneous interventional treatment of CTOs, such as stiffer guidewires, low-profile balloons, laser light emitting wires, atherectomy devices, drills, drug eluting stents, and re-entry catheters. The factor that is most determinative of whether the physician can successfully recanalize a CTO is the physician's ability to advance a suitable guidewire from a position within the true lumen of the artery proximal to the CTO lesion, across the CTO lesion, i.e., either through the lesion or around it, and then back into the true lumen of the artery at a location distal to the CTO lesion.

In some cases, such as where the artery is totally occluded by hard, calcified atherosclerotic plaque, the guidewire may tend to deviate to one side and penetrate through the intima of the artery, thereby creating a neo-lumen called a "subintimal tract," i.e., a penetration tract formed within the wall of the artery between the intima and adventitia. In these cases, the distal end of the guidewire may be advanced to a position distal to the lesion but remains trapped within the subintimal tract. In such instances, it is then necessary to direct or steer the guidewire from the subintimal tract back into the true lumen of the artery at a location distal to the CTO lesion. The process of manipulating the guidewire to reenter the artery lumen is often difficult and various solutions have been proposed utilizing means for handling such a reentry operation.

As well a number of catheter-based devices have been heretofore suggested for redirecting subintimally placed guidewires or other medical devices back into the true lumen of the artery. Included among these are a variety of catheters having laterally deployable cannulae, i.e., hollow needles. For example, the PIONEER® catheter system by Medtronic, Inc. utilizes a penetrator or needle that exits through a side exit port of the catheter to puncture the intimal layer distal of the CTO to re-enter the true lumen of the vessel. A second guidewire is then passed through the laterally deployed needle and is advanced into the true lumen of the artery. However, a need in the art still exists for other medical devices or systems that consistently and reliably direct guidewires or other devices tracked within the subintimal space of a vessel back into the true lumen of the vessel for the treatment of a CTO.

BRIEF SUMMARY OF THE INVENTION

Embodiments hereof are directed to apparatuses for bypassing an occlusion in a blood vessel. In an embodiment, the apparatus includes a shaft component defining a lumen that extends from a proximal end to a distal end thereof and having a distal tip portion that is bendable relative to a proximal portion thereof and a needle component configured to be slidably disposed within the shaft component lumen and removable therefrom. The needle component includes a proximal segment and an angled distal tip segment, wherein in a first configuration of the apparatus the angled distal tip segment of the needle component is held in a straightened form within the shaft component and wherein in a second configuration the angled distal tip segment of the needle component bends the distal tip portion of the shaft component away from a longitudinal axis of the proximal portion. In embodiments hereof, a balloon is mounted on a distal portion of the shaft component and is utilized to anchor and stabilize the occlusion bypassing apparatus within a subintimal tract of a vessel.

In another embodiment, the apparatus includes an outer shaft component, an inner shaft component and a needle component. The outer shaft component defines a lumen that extends from a proximal end to a distal end thereof and has a balloon mounted on a distal portion thereof. The inner shaft component is configured to be slidably and rotatably disposed within the outer shaft component lumen and removable therefrom, and the inner shaft component defines a lumen that extends from a proximal end to a distal end thereof. The needle component is configured to be slidably disposed within the inner shaft component lumen and removable therefrom, the needle component having a proximal segment and an angled distal tip segment. In a first configuration of the apparatus, the angled distal tip segment of the needle component is held in a straightened form within the inner and outer shaft components. In a second configuration of the apparatus, when a distal portion of the inner shaft component extends from the distal end of the outer shaft component with at least a portion of the angled distal tip segment of the needle component concurrently disposed therein, the angled distal tip segment of the needle component bends the distal portion of the inner shaft component away from a longitudinal axis of the apparatus.

Embodiments hereof also relate to methods for bypassing an occlusion in a blood vessel having a subintimal tract formed in a wall of the vessel adjacent to the occlusion. In one such method, a guidewire is advanced through the subintimal tract from a near or proximal side of the occlusion to a position where a distal end of the guidewire is positioned in the subintimal tract on a far or distal side of the occlusion. A balloon catheter is advanced through the subintimal tract over the guidewire until a distal portion of the catheter is disposed at the distal side of the occlusion. Once so positioned a balloon of the balloon catheter is inflated to anchor the balloon catheter within the subintimal tract. An elongate needle component is advanced in a straightened configuration relative to the balloon catheter until a distal tip segment of the needle component extends from a distal end of the balloon catheter. Thereafter, the needle component is permitted to return to an angled configuration in which the distal tip segment bends away from a longitudinal axis of a proximal portion of the needle component, wherein at least the distal tip segment of the needle component has a shape memory to return the needle component to the angled configuration. In an embodiment, the needle component is held in the straightened configuration by an elongate stylet that extends therethrough. In another embodiment, the needle component is held in the straightened configuration by a reinforced segment of the shaft component.

In another embodiment for bypassing an occlusion in a blood vessel having a subintimal tract formed in a wall of the vessel adjacent to the occlusion, an outer shaft component of an occlusion bypassing apparatus is advanced over an indwelling guidewire until a distal portion of the outer shaft component is disposed at the distal side of the occlusion. An inner shaft component and a needle component of the occlusion bypassing apparatus are loaded within the outer shaft component until a distal portion of the inner shaft component is disposed within the distal portion of the outer shaft component, wherein the needle component is slidably disposed within the inner shaft component in a straight configuration. A balloon mounted on the occlusion bypassing apparatus is then inflated to anchor the occlusion bypassing apparatus within the subintimal tract. The needle component of the occlusion bypassing apparatus is advanced relative to the inner shaft component until at least a portion of an angled distal tip segment of the needle component is disposed within the distal portion of the inner shaft component that extends from a distal end of the outer shaft component to thereby bend the distal portion of the inner shaft component away from a longitudinal axis of the occlusion bypassing apparatus.

In another embodiment for bypassing an occlusion in a blood vessel having a subintimal tract formed in a wall of the vessel adjacent to the occlusion, an occlusion bypassing apparatus having a shaft component and a needle component is advanced through the subintimal tract over an indwelling guidewire until a distal end of the occlusion bypassing apparatus is disposed at the distal side of the occlusion. The needle component is slidably disposed within the shaft component and defines a lumen through which the guidewire extends. A balloon of the occlusion bypassing apparatus is inflated to anchor the occlusion bypassing apparatus within the subintimal tract. The needle component of the occlusion bypassing apparatus is advanced relative to the shaft component until at least a portion of an angled distal tip segment of the needle component is disposed within a distal portion of the shaft component to thereby bend the distal portion of the shaft component away from a longitudinal axis of the occlusion bypassing apparatus.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of an occlusion bypassing apparatus according to an embodiment hereof, wherein configuration a distal end of an outer shaft component is shown in partial section.

FIG. 1A is a cross-sectional view of the occlusion bypassing apparatus of FIG. 1 taken along line A-A thereof.

FIG. IAA is a cross-sectional view of an occlusion bypassing apparatus of FIG. 1 taken along line A-A thereof depicting an outer shaft component in accordance with another embodiment hereof.

FIG. 2 is a side view of a distal portion of the occlusion bypassing apparatus of FIG. 1, wherein a distal portion of an inner shaft component of the apparatus is in a bent configuration.

Figure 2A:
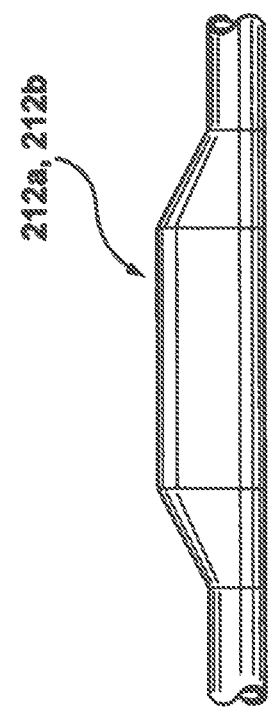
Figure 2B:
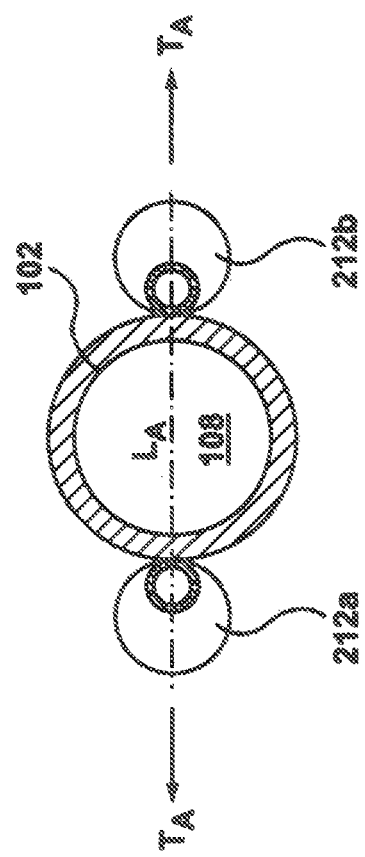

FIG. 2A depicts a balloon having an asymmetrical inflated configuration in accordance with another embodiment hereof FIG. 2B depicts a cross-sectional view of a shaft component that utilizes balloons as shown in FIG. 2A in accordance with another embodiment hereof.

FIG. 3 is a side view of the distal portion of the occlusion bypassing apparatus shown in FIG. 2, wherein a needle component of the apparatus extends from the inner shaft component.

FIG. 4A is a side view of an outer shaft component of the occlusion bypassing apparatus of FIG. 1 in accordance with an embodiment hereof.

FIG. 4B is a side view of an inner shaft component of the occlusion bypassing apparatus of FIG. 1 in accordance with an embodiment hereof.

FIG. 4BB is a cross-sectional view of the inner shaft component of FIG. 4B taken along line BB-BB thereof.

Figure 4C:
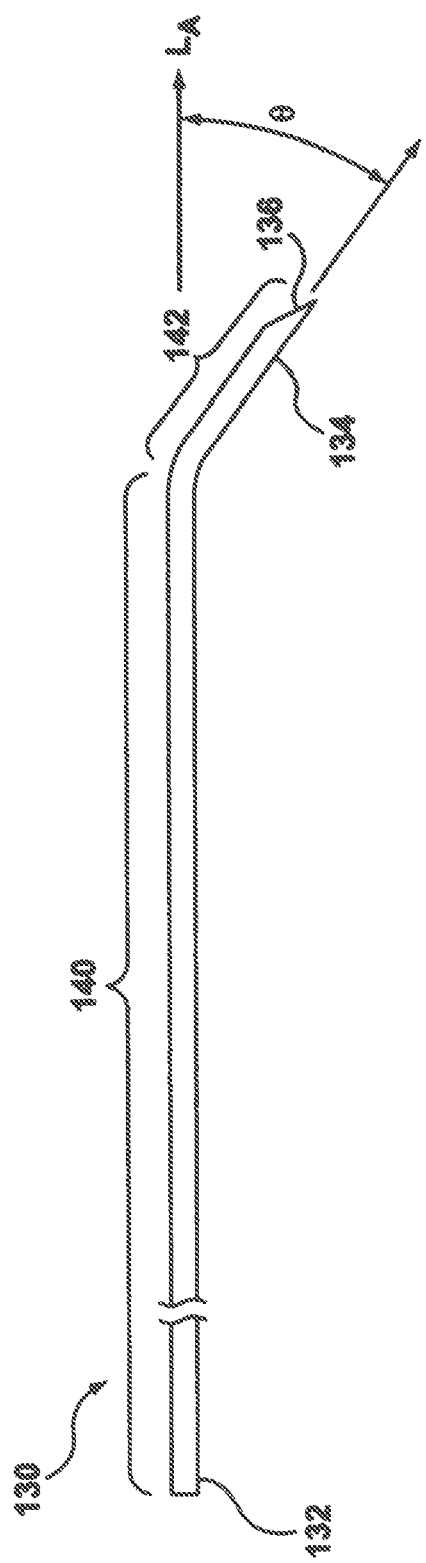
Figure 4D:
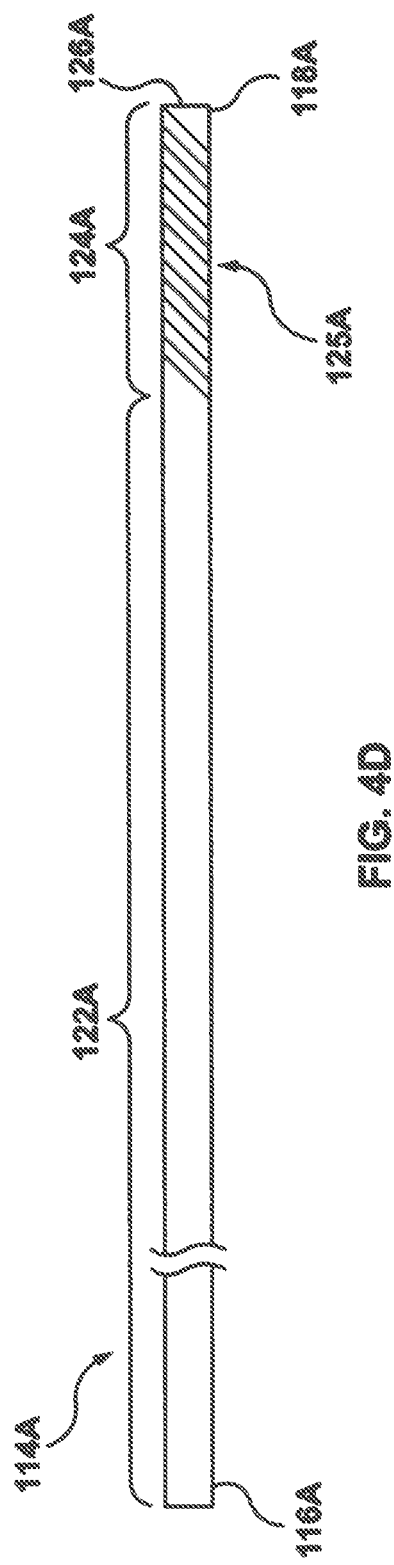

FIG. 4C is a side view of a needle component of the occlusion bypassing apparatus of FIG. 1 in accordance with an embodiment hereof FIG. 4D is a side view of an alternative embodiment of an inner shaft component of the occlusion bypassing apparatus of FIG. 1.

FIG. 5 is a side view of an occlusion bypassing apparatus according to another embodiment hereof.

FIG. 6 is a side view of a needle component of the occlusion bypassing apparatus of FIG. 5 in accordance with an embodiment hereof FIG. 7 is a side view of a stiffening stylet of the occlusion bypassing apparatus of FIG. 5 in accordance with an embodiment hereof FIG. 8A is a side view of a subassembly of the needle component and stylet of FIGS. 6 and 7 with the stylet fully inserted to extend through the needle component such that the needle component is held in a substantially straightened form by the stylet.

FIG. 8B is a side view of the subassembly in FIG. 8A with the stylet partially retracted from the needle component such that the needle component is permitted to bend.

FIG. 8C is a side view of the needle component as shown in FIG. 8A returned to its shape memory bent configuration after the stylet has been removed.

Figure 9:
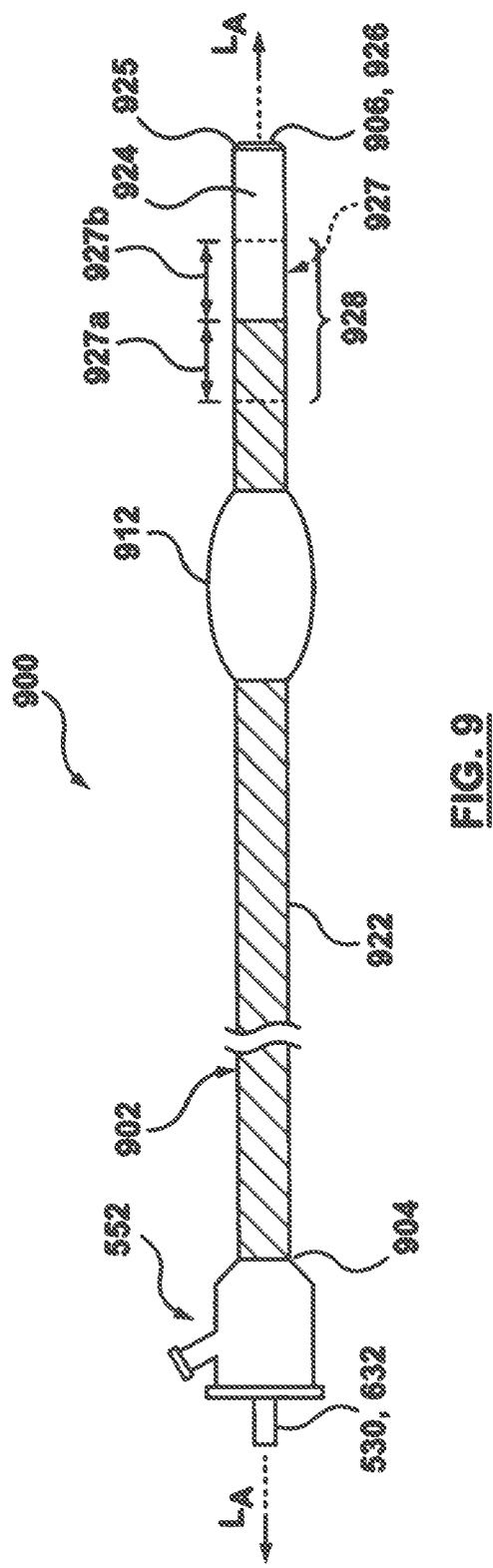

FIG. 9 is a side view of an occlusion bypassing apparatus according to another embodiment hereof.

Figure 10:
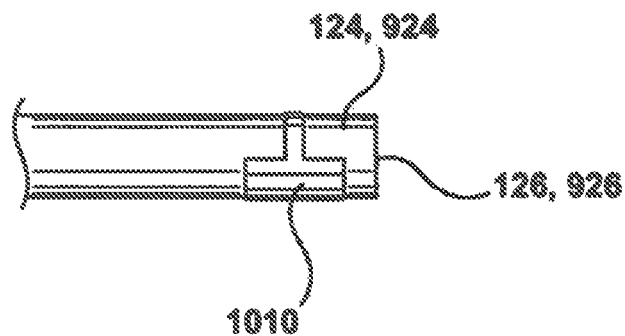

FIG. 10 depicts a side view of a distal end of an occlusion bypassing apparatus in accordance with embodiments hereof with an exemplary radiopaque marker attached thereto.

Figure 10A:
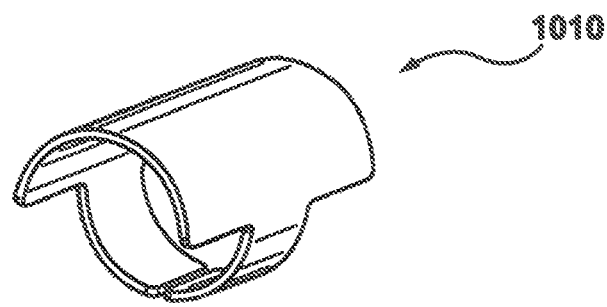

FIG. 10A is a perspective view of the exemplary radiopaque marker shown in FIG. 10.

Figure 11:
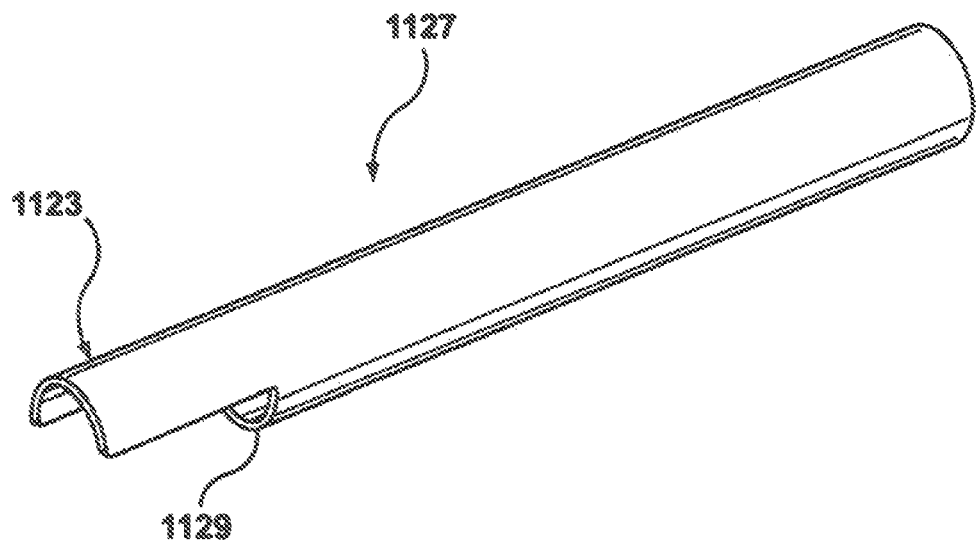

FIG. 11 is a perspective view of a metallic shaft segment in accordance with an embodiment hereof.

Figure 12:
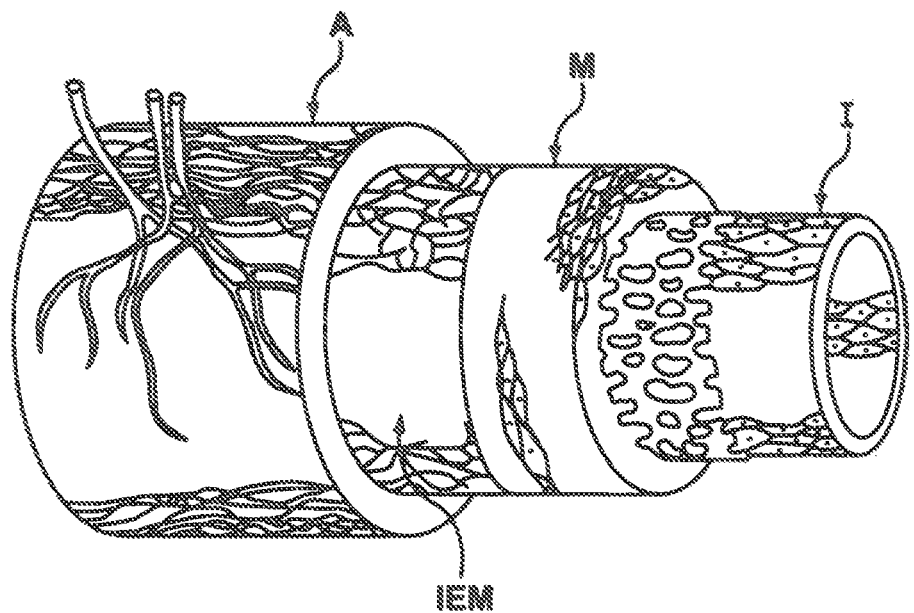

FIG. 12 is a diagram of an artery showing the three layers of tissue that comprise the artery wall.

FIGS. 13-23 illustrate the steps of utilizing the occlusion bypassing apparatus of FIG. 1 to bypass a chronic total occlusion according to an embodiment hereof.

FIGS. 24-29 illustrate the steps of utilizing the occlusion bypassing apparatus of FIG. 1 to bypass a chronic total occlusion according to another embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The term "shape memory" is used in the following description with reference to the needle components hereof and is intended to convey that the structures are shaped or formed from a material that can be provided with a mechanical memory to return the structure from a straightened delivery configuration to an angled or bent deployed configuration. Non-exhaustive exemplary materials that may be imparted with a shape memory include stainless steel, a pseudo-elastic metal such as a nickel titanium alloy or nitinol, or a so-called super alloy, which may have a base metal of nickel, cobalt, chromium, or other metal. Shape memory may be imparted to a tubular or rod-like structure by thermal treatment to achieve a spring temper in stainless steel, for example, or to set a mechanical memory in a susceptible metal alloy, such as nitinol.

The following detailed description is merely exemplary in nature and is not intended to limit the invention or the application and uses of the invention. Although the description of the invention is in the context of treatment of blood vessels such as smaller diameter peripheral or coronary arteries, the invention may also be used in any other body passageways where it is deemed useful. Although the description of the invention generally refers to a system and method of bypassing a vessel blockage in a proximal-to-distal direction, i.e. antegrade or with the blood flow, the invention may be used equally well to bypass a vessel blockage in a distal-to-proximal direction, i.e. retrograde or against the blood flow if access is available from that direction. In other terms, the system and method described herein may be considered to bypass a vessel blockage from a near side of the blockage to a far side of the blockage. Furthermore, there is no intention to be bound by any expressed or implied theory presented in the preceding technical field, background, brief summary or the following detailed description.

Embodiments hereof relate to a system and method for re-entering the true lumen of a vessel after subintimally bypassing an occlusion in a blood vessel such as a chronic total occlusion (CTO) of an artery. FIG. 1 illustrates the main components of occlusion bypassing apparatus 100, which are separately shown in FIGS. 4A-4C, assembled one within the other with a distal portion 124 of an inner shaft component 114 extending from a distal end 106 of an outer shaft component 102. More particularly with reference to FIGS. 1 and 4A-4C, an occlusion bypassing apparatus 100 includes an outer shaft component 102 with a balloon 112 for stabilization or anchoring the occlusion bypassing apparatus, an inner shaft component 114 slidably and rotatably disposed within outer shaft component 102, and a needle component 130 disposed within inner shaft component 114. Needle component 130 is utilized to selectively bend or curve distal portion 124 of inner shaft component 114, as shown in FIGS. 2 and 3, in order to position or extend distal portion 124 of inner shaft component 114 towards the true lumen of a vessel, as will be explained in more detail herein. While occlusion bypassing apparatus 100 is stabilized within a subintimal space of a vessel, needle component 130 is advanced to bend or bow distal portion 124 of inner shaft component 114, and thereafter, if required, needle component 130 and inner shaft component 114 may be jointly or collectively rotated to orient a distal opening 126 of inner shaft component distal portion 124 towards the true lumen of the vessel. Needle component 130 also provides the required stiffness to occlusion bypassing apparatus 100 for re-entering the true lumen of the vessel. In FIG. 2 a distal tip 136 of needle component 130, which is visible in FIGS. 3 and 4C, is disposed within and bends distal portion 124 of inner shaft component 114 in a configuration suitable for rotation of the two components within the subintimal space of the vessel wall. In FIG. 3 distal tip 136 is exposed to distally extend from distal opening 126 of inner shaft component 114 in a configuration that is suitable for puncturing the vessel wall to gain access to the true lumen.

With reference to FIGS. 1, 1A and 4A-4C, outer shaft component 102 is an elongate tubular or cylindrical element defining a lumen 108 that extends from a proximal end 104 to a distal end 106 thereof and has balloon 112 mounted on a distal portion thereof. In an embodiment, outer shaft component may be sized to be used with a 5F introducer sheath with lumen 108 being sized to accommodate a guidewire having an outer diameter of 0.035 inch. Proximal end 104 of outer shaft component 102 extends out of the patient and is coupled to a first hub 152. An inflation shaft or tube 148 defining an inflation lumen 150 extends through lumen 108 of outer shaft component 102 to allow inflation fluid received through Luer fitting 154 of first hub 152 to be delivered to balloon 112. FIG. 1AA is a cross-sectional view of an occlusion bypassing apparatus of FIG. 1 taken along line A-A thereof depicting an outer shaft component 102AA in accordance with another embodiment hereof, wherein the outer shaft component 102AA includes an inflation shaft or tube 148AA defining an inflation lumen 150AA that is attached to extend along an outer surface of outer shaft component 102AA to allow inflation fluid received through Luer fitting 154 of first hub 152 to be delivered to balloon 112. In accordance with an embodiment hereof, the combined structures of outer shaft component 102, balloon 112 and hub 152 as described herein may be considered to comprise a balloon catheter. It would also be understood by one of ordinary skill in the art of balloon catheter design that hub 152 includes a proximal port 156 with a hemostatic valve to accommodate insertion of other components of occlusion bypassing apparatus 100 into outer shaft component 102, and that Luer fitting 154, or some other type of fitting, may be connected to a source of inflation fluid (not shown) and may be of another construction or configuration without departing from the scope of the present invention. Other types of construction are also suitable for outer shaft component 102, such as, without limitation thereto, a catheter shaft having a central lumen and an inflation lumen formed by multi-lumen profile extrusion. When inflated, balloon 112 anchors occlusion bypassing apparatus 100 within the anatomy, more particularly within the subintimal space of the vessel wall when utilized in the treatment of a CTO, so as to provide stability thereto.

Outer shaft component 102 and inflation shaft 148 may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, outer shaft component 102 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of outer shaft component 102 may be formed from a reinforced polymeric tube. In accordance with an embodiment hereof, balloon 112 may radially inflate uniformly so as to have a symmetric expanded configuration about the longitudinal axis $L_A$ of occlusion bypassing apparatus 100, as shown in FIGS. 2 and 3. In accordance with another embodiment hereof, balloons 212a, 212b having an asymmetric expanded configuration relative to the longitudinal axis $L_A$ of occlusion bypassing apparatus 100 may be used for anchoring and stabilizing the apparatus within the subintimal space, as shown in FIG. 2A. With reference to the dual balloon arrangement depicted in FIG. 2B, balloons 212a, 212b primarily expand in opposite directions to each other along an axis $T_A$ transverse to the longitudinal axis $L_A$ of occlusion bypassing apparatus 100 to thereby provide a flatter somewhat oval cross-section to the apparatus when inflated. In accordance with embodiments hereof, balloons 112, 212a, 212b may be formed of any suitable polymeric material used for dilatation balloon manufacturing, for instance, polyether block amide (PEBA) and polyurethane (PU), and may have an outer diameter in the range of 2-4 mm and a length in the range of 5-15 mm.

Inner shaft component 114 is an elongate tubular or cylindrical element that is configured to be slidably and rotatably disposed within lumen 108 of outer shaft component 102 and removable therefrom. As used herein, "slidably" denotes back and forth movement in a longitudinal direction while "rotatably" denotes movement or rotation about a longitudinal axis $L_A$ of the occlusion bypassing apparatus 100. As best shown in FIG. 4B, in one embodiment hereof, inner shaft component 114 includes a first or proximal portion 122, a second or distal portion 124, and a reinforced intermediate portion 128 disposed or sandwiched between proximal and distal portions 122, 124. Distal portion 124 of inner shaft component 114 may include a radiopaque marker 110 coupled thereto in order to visually monitor the position thereof. Proximal portion 122, intermediate portion 128, and distal portion 124 collectively define a continuous lumen 120 that extends from a proximal end 116 to a distal end 118 of inner shaft component 114. Lumen 120 extends substantially the entire length of the catheter for accommodating needle component 130. Proximal end 116 of inner shaft component 114 is coupled to a second hub 160 having a proximal port 162 with a hemostatic valve, and is disposed within strain relief element 158 that is attached to distally extend from second hub 160.

In accordance with embodiments hereof, proximal portion 122 is a tubular or cylindrical shaft segment having a first flexibility, distal portion 124 is a tubular or cylindrical shaft segment having a second flexibility, and intermediate portion 128 is a tubular or cylindrical shaft segment having a third flexibility with intermediate portion 128 being less flexible or stiffer than proximal and distal portions 122, 124. In the embodiment shown in FIGS. 4B and 4BB, proximal portion 122 is an elongate polymeric tube having a reinforcement layer, distal portion 124 is a polymeric tube that is more flexible than the proximal portion, and intermediate portion 128 includes a metallic shaft segment 127, such as a short length of a metallic hypotube, having a proximal half 127a embedded within a distal end of proximal portion 122 and a distal half 127b overlapped by a proximal end of distal portion 124. In other words, intermediate portion 128 of the embodiment of FIG. 4B includes the metallic shaft segment 127 and segments of proximal and distal portions 122, 124 that overlap therewith.

Proximal and distal portions 122, 124 may be formed from any suitable polymeric material for forming a medical device, such as polyethylene terephthalate (PET), polypropylene, polyamide, polyethylene, polyether block amide (PEBA), fluoropolymers such as polytetrafluoroethylene (PTFE) or fluorinated ethylene propylene (FEP), or combinations thereof, with the material for forming distal portion 124 being one that is more flexible than the material of proximal portion 122 so that distal portion 124 may be readily bent or curved via needle component 130 as described herein. In an embodiment, for example, the proximal and distal portions 122, 124 may both be formed from the same soft polymeric material, such as polyether block amide (PEBA) or a standard polyamide such as Nylon 12 or Nylon 66, with a reinforcing mesh, braid or wire layer being incorporated within the polymeric material of proximal portion 122 in order to enhance the column strength thereof. In another embodiment, proximal portion 122 and distal portion 124 may be formed from different polymeric materials having different flexibilities with proximal portion 122 being formed from a first material, such as stainless steel braid embedded in PEBAX® 7233, and distal portion 124 being formed from a second material, such as PEBAX® 5533, that is more flexible than the first material. In accordance with embodiments hereof, reinforced intermediate portion 128 may be formed by embedding metallic shaft segment 127, for e.g., of stainless steel or nitinol, within the polymeric material of one of the proximal and distal portions of the inner shaft component 114. In an embodiment, proximal half 127a of metallic shaft segment 127 may be glued to or embedded in proximal portion 122 with distal half 127b of metallic shaft segment 127 being fit within distal portion 124.

FIG. 4D illustrates another embodiment of an inner shaft component 114A that may be used instead of inner shaft component 114 in the occlusion bypassing apparatus 100 of FIG. 1. Inner shaft component 114A includes a first or proximal portion 122A and a second or distal portion 124A. Proximal portion 122A and distal portion 124A collectively define a continuous lumen (not shown) that extends from a proximal end 116A to a distal end 118A of inner shaft component 114A. In this embodiment, inner shaft component 114A is a continuous metallic hypotube. Distal portion 124A includes a spiral cut segment 125A so that distal portion 124A is more flexible than proximal portion 122A. The spiral cut or slit through a sidewall of distal portion 124A increases the flexibility thereof so that distal portion 124A may be readily bent or curved via needle component 130 as will be described in more detail herein.

Needle component 130 is an elongate tubular or cylindrical element that is configured to be slidably disposed within lumen 120 of inner shaft component 114 and removable therefrom. More particularly, needle component 130 is disposed within inner shaft component 114 such that there is sufficient space or room therebetween for needle component 130 to be moved or slidable in a longitudinal direction relative to inner shaft component 114. In other words, there is not a tight interference or friction fit between needle component 130 and inner shaft component 114. However, needle component 130 is disposed within inner shaft component 114 such that inner shaft component 114 rotates or spins with rotation of needle component 130. In other words, when needle component 130 is rotated by a clinician, needle component 130 contacts an inner surface of inner shaft component 114 and thereby rotates inner shaft component 114. The two components may rotate simultaneously as an ensemble structure, or they may rotate independently. In an embodiment, a removable locking device or wire torquer may be utilized at the proximal ends of the needle and inner shaft components during rotation thereof, wherein the locking device or wire torquer may then be removed when the needle component is required to be moved relative to the inner shaft component in a longitudinal direction.

In order to accommodate a guidewire, needle component 130 may be a hypotube that defines a lumen 138 therethrough from a proximal end 132 to a distal end 134 of the needle component. Proximal end 132 extends out of the patient from second hub 160 to be manipulated by a clinician and distal end 134 includes a distal tip 136 configured to pierce or penetrate through a wall of a vessel. In an embodiment, lumen 138 of needle component 130 is sized to accommodate a guidewire having an outer diameter equal to or less than 0.014 inch such that occlusion bypassing apparatus 100 has a low profile.

As best shown in FIG. 4C, needle component 130 has an elongated first or proximal segment 140 and a second or distal angled tip segment 142 so as to have an angled or bent configuration. More particularly, as shown in FIG. 4C, angled distal tip segment 142 extends, bends, or otherwise curves at an acute angle θ relative to a longitudinal axis of elongated proximal segment 140 and in turn relative to the longitudinal axis $L_A$ of occlusion bypassing apparatus 100. In embodiments hereof, angle θ may be in the range of 30° to 80°. In an embodiment at least angled distal tip segment 142 of needle component 130 is formed from a biocompatible resilient metal such as spring temper stainless steel or nitinol, which utilizes the elastic properties of stress induced martensite, such that a heat or thermal treatment of the selected material may be used to set the shape memory of angled distal tip segment 142. In an embodiment, needle component 130 may be formed from more than one material, for e.g., with an elongated proximal segment 140 being formed of stainless steel and only angled distal tip segment 142 being formed of nitinol.

In a first configuration of occlusion bypassing apparatus 100 shown in FIG. 1, angled distal tip segment 142 of needle component 130 is restrained or held in a straightened form within intermediate portion 128 of inner shaft component 114, which is formed from a relatively stiff or less flexible material as described above in order to effectively straighten the angled distal tip segment. In the first configuration, flexible distal portion 124 of inner shaft component 114 may distally extend from distal end 106 of outer shaft component 102, as shown in FIG. 1, or may be disposed within distal end 106 of outer shaft component 102.

In a second configuration of occlusion bypassing apparatus 100 shown in FIG. 2, distal portion 124 of inner shaft component 114 distally extends from distal end 106 of outer shaft component 102 and needle component 130 is distally advanced relative to inner shaft component 114 such that angled distal tip segment 142 is no longer constrained by intermediate portion 128 of inner shaft component 114. Balloon 112 may be expanded or inflated to anchor outer shaft component 102 within a subintimal tract either before or after the distal advancement of needle component 130. When released from intermediate portion 128, angled distal tip segment 142 resumes its shape memory geometry by its own internal restoring forces and concurrently bends, curves, or bows flexible distal portion 124 of inner shaft component 114 away from the longitudinal axis $L_A$ of occlusion bypassing apparatus 100 such that flexible distal portion 124 of inner shaft component 114 extends at acute angle θ relative to the longitudinal axis $L_A$ of occlusion bypassing apparatus 100, as shown in FIGS. 2 and 3. As described with respect to FIG. 4C, angle θ may be in the range of 30° to 80°. Bending of distal portion 124 of inner shaft component 114 permits a user or clinician to orient distal opening 126 of distal portion 124 of inner shaft component 114 towards a true lumen of a vessel as described herein. The position of distal portion 124 of inner shaft component 114 during bending thereof may be monitored via marker 110 thereon.

In another embodiment hereof, inner shaft component 114 of occlusion bypassing apparatus 100 does not include a reinforced intermediate portion 128 having a metallic shaft segment 127. In such an embodiment, the combination or subassembly of outer shaft component 102 and inner shaft component 114 has a sufficient stiffness or rigidity to hold the angled distal tip segment 142 of needle component 130 in a straightened position when the angled distal tip segment 142 is concurrently disposed within both outer shaft component 102 and inner shaft component 114. The angled distal tip segment 142 then resumes its bent shape, as shown in FIGS. 2 and 3, when flexible distal portion 124 of inner shaft component 114 is distally extended relative to outer shaft component 102.

Distal tip 136 of needle component 130 is disposed within inner shaft component 114, as shown in FIG. 2, during rotation of inner shaft component 114 and needle component 130. Once distal opening 126 of inner shaft component 114 is positioned in the direction of the true lumen of the vessel, distal tip 136 of needle component 130 is extended to distally protrude from distal opening 126 of inner shaft component 114, while distal tip segment 142 of needle component 130 still bends distal portion 124 of inner shaft component 114 away from longitudinal axis $L_A$ of occlusion bypassing apparatus 100. When needle component 130 is distally advanced or extended as shown in FIG. 3, distal tip 136 may be used to penetrate through the vessel wall and re-enter a true lumen of a vessel as described herein.

FIG. 5 depicts an occlusion bypassing apparatus 500 in accordance with another embodiment hereof. Occlusion bypassing apparatus 500 includes a shaft component 502 that defines a through lumen from a proximal end 504 to a distal end 506 thereof through which a subassembly of a needle component 530 and a stiffening stylet 531, shown unassembled in FIGS. 6 and 7, are slidably and rotatably disposed. As well the through lumen of shaft component 502 will accommodate a guidewire therethrough and may contain a separate guidewire lumen. Shaft component 502 includes a proximal shaft portion 522 and a distal shaft portion 524 with a balloon 512 being secured to extend from an outer surface thereof. Proximal end 504 of shaft component 502 is coupled to a hub 552 that includes a Luer fitting 554 for delivering an inflation fluid to balloon 512 via an inflation lumen (not shown) of shaft component 502 and a proximal port 556 for permitting insertion and manipulation of the needle component 530 and stylet 531 subassembly therethrough. The combined structures of shaft component 502, balloon 512 and hub 552 as described herein may be considered to comprise a balloon catheter in accordance with an embodiment hereof. One of ordinary skill in the art of balloon catheter design will appreciate that hub 552 may include another type of fitting that may be connected to a source of inflation fluid (not shown) and may be of another construction or configuration without departing from the scope of the present invention.

As similarly described with reference to formation of outer shaft component 102 of the previous embodiment, proximal and distal shaft portions of shaft component 502 may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, shaft component 502 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of shaft component 502 may be formed from a reinforced polymeric tube with distal shaft portion 524 being formed to have or include an atraumatic tip 525 of occlusion bypassing apparatus 500.

Needle component 530 is configured to be slidably and rotatably disposed within the lumen of shaft component 502 and defines a lumen that extends from a proximal end 632 to a distal end 636 thereof for receiving stylet 531 therein. Needle component 530 has an elongated first or proximal segment 640 and a second or distal angled tip segment 642, as shown in FIG. 6. Angled distal tip segment 642 has a bent or curved configuration that extends, bends, or otherwise curves at an acute angle θ relative to elongated proximal segment 640 and relative to longitudinal axis $L_A$ of occlusion bypassing apparatus 500. In embodiments hereof, angle θ may be in the range of 30° to 80°. Needle component proximal end 632 proximally extends from hub proximal port 556 to be accessible by a clinician and needle component distal end 636 includes a tip configured to pierce or penetrate through a wall of a vessel.

As similarly described with reference to formation of needle component 130 of the previous embodiment, at least angled distal tip segment 642 of needle component 530 is formed of a biocompatible resilient metal such as spring temper stainless steel or nitinol, which utilizes the elastic properties of stress induced martensite, such that a heat or thermal treatment of the selected material may be used to provide a shape set or shape memory to angled distal tip segment 642. In an embodiment, needle component 530 may be a hypotube of spring temper stainless steel or nitinol with a distal end that has been shape set in an angled configuration. In another embodiment, needle component 530 may be formed from more than one material, e.g., with elongated proximal segment 640 being formed of stainless steel and only angled distal tip segment 642 being formed of nitinol to have a shape memory.

The lumen of needle component 530 is sized to slidably accommodate stylet 531 therein. With reference to FIGS. 7, and 8A-8C, stylet 531 is an elongate wire structure having a proximal end 733 and a distal end 735 with a length and diameter that are sized to extend through needle component 530 such that when stylet 531 is inserted therein angled distal tip segment 642 is thereby straightened, as shown in FIG. 8A. When needle component 530 is held in a straightened configuration by stylet 531 as shown in FIG. 8A, the subassembly may be readily loaded within and distally advanced relative to shaft component 502. In addition, once the subassembly is loaded and fully advanced through shaft component 502, needle component 530 may be distally advanced relative to both stylet 531 and shaft component 502 to thereby in a controlled manner gradually return distal tip segment 642 to its shape set curved configuration. With reference to FIG. 8B, needle component 530 is shown having been distally advanced relative to stylet 531 to a point where distal tip segment 642 begins to bend, with stylet 531 still extending therein. With reference to FIG. 8C, needle component 530 is shown after stylet 531 has been fully removed such that distal tip segment 642 has fully returned to its shape set curved configuration.

FIG. 9 depicts an occlusion bypassing apparatus 900 in accordance with another embodiment hereof. Occlusion bypassing apparatus 900 includes a shaft component 902 that defines a lumen from a proximal end 904 to a distal end 906 thereof through which a needle component, such as previously described needle component 530, is slidably and rotatably disposed. Shaft component 902 includes a proximal shaft portion 922, a reinforced intermediate shaft portion 928 and a distal shaft portion 924 with a balloon 912 being secured to extend from an outer surface of the proximal shaft portion 922. Proximal end 904 of shaft component 902 is coupled to a hub, such as previously described hub 552, that includes a Luer fitting for delivering an inflation fluid to balloon 912 via an inflation lumen (not shown) of shaft component 902 and a proximal port for permitting insertion and manipulation of needle component 530 therethrough, The combined structures of shaft component 902, balloon 912 and hub 552 as described herein may be considered to comprise a balloon catheter in accordance with an embodiment hereof.

In the embodiment shown in FIG. 9, proximal shaft portion 922 is an elongate polymeric tube having a reinforcement layer, distal shaft portion 924 is a polymeric tube that is more flexible than the proximal shaft portion, and intermediate shaft portion 928 includes a short metallic shaft segment 927 having a proximal half 927a embedded within a distal end of proximal shaft portion 922 and a distal half 927b overlapped by a proximal end of distal shaft portion 924. More particularly as similarly described with reference to the formation of inner shaft component 114 of occlusion bypassing apparatus 100, proximal and distal shaft portions 922, 924 of shaft component 902 may be formed from any suitable polymeric material for forming a medical device, such as polyethylene terephthalate (PET), polypropylene, polyamide, polyethylene, polyether block amide (PEBA), fluoropolymers such as polytetrafluoroethylene (PTFE) or fluorinated ethylene propylene (FEP), or combinations thereof, with the material for forming distal shaft portion 924 being one that is more flexible than the material of proximal shaft portion 922 so that distal shaft portion 924 forms an atraumatic tip 925 of occlusion bypassing apparatus 900 and so that distal shaft portion 924 may be readily bent or curved via needle component 530 as described herein. In an embodiment, for example, the proximal and distal shaft portions 922, 924 may both be formed from the same soft polymeric material, such as polyether block amide (PEBA) or a standard polyamide such as Nylon 12 or Nylon 66, with a reinforcing metallic mesh, braid or wire layer being incorporated within the polymeric material of proximal shaft portion 922 in order to enhance the column strength thereof. In another embodiment, proximal shaft portion 922 and distal shaft portion 924 may be formed from different polymeric materials having different flexibilities with proximal shaft portion 922 being formed from a first material, such as stainless steel braid embedded in PEBAX® 7233, and distal shaft portion 924 being formed from a second material, such as PEBAX® 5533, that is more flexible than the first material. In accordance with embodiments hereof, intermediate shaft portion 928 may be formed by embedding metallic shaft segment 927, e.g., of stainless steel or nitinol, within the polymeric material of one of the proximal and distal portions of the shaft component 922. In an embodiment, a proximal half 927a of metallic shaft segment 927 may be glued to or embedded in proximal shaft portion 922 with a distal half 927b of metallic shaft segment 927 being fit within distal shaft portion 924.

In FIG. 9 occlusion bypassing apparatus 900 is depicted with needle component 530 loaded and in a straightened form within shaft component 902 such that the apparatus as shown may be advanced over a guidewire to a treatment site. In an embodiment, the guidewire may be slidably received through the lumen of needle component 530. More particularly, angled distal tip segment 642 of needle component 530 is restrained or held in a straightened form within intermediate shaft portion 928 of shaft component 902, which is formed from a relatively stiff or less flexible material as described above in order to effectively straighten the angled distal tip segment. Once occlusion bypassing apparatus 900 has been tracked through the subintimal tract or space such that distal tip 925 is properly positioned at the treatment site, needle component 530 is distally advanced relative to shaft component 902 such that angled distal tip segment 642 is no longer constrained by intermediate shaft portion 928. Balloon 912 may be expanded or inflated to anchor shaft component 902 within the subintimal tract either before or after the distal advancement of needle component 530. When released from intermediate shaft portion 928, angled distal tip segment 642 resumes its shape memory geometry by its own internal restoring forces and concurrently bends, curves, or bows flexible distal shaft portion 924 away from the longitudinal axis $L_A$ of occlusion bypassing apparatus 900 such that flexible distal shaft portion 924 extends at acute angle relative to the longitudinal axis $L_A$ of occlusion bypassing apparatus 900, as similarly described with reference to inner shaft component 114 of occlusion bypassing apparatus 100 shown in FIGS. 2 and 3. Bending of distal shaft portion 924 permits a user or clinician to orient an opening 926 at shaft component distal end 906 towards a true lumen of a vessel as described herein.

In accordance with embodiments hereof during positioning of the distal openings 126, 926 of occlusion bypassing apparatus 100, 900 such that the openings are directed toward the true lumen of a vessel, the position of distal portion 124 of inner shaft component 114 of occlusion bypassing apparatus 100 and the position of distal shaft portion 924 of shaft component 902 of occlusion bypassing apparatus 900 may include a radiopaque marker, such as radiopaque marker 1010 shown in FIGS. 10 and 10A, to permit visualization thereof under fluoroscopic imaging techniques. In alternate embodiments hereof to monitor the positioning of the distal openings 126, 926 of occlusion bypassing apparatus 100, 900, a metallic shaft segment 1127 of FIG. 11 may be used within embodiments hereof that include an intermediate portion 128 or intermediate shaft portion 928. Metallic shaft segment 1127 is of a material that may be visualized under fluoroscopic imaging techniques and includes an orienting geometry, such as hemispherical protrusion 1123, at a distal end 1129 thereof that may be used by the clinician to assure proper positioning.

FIG. 12 is a sectional view of the anatomy of an artery wall, which for purposes of this description is shown to consist essentially of three layers, the tunica intima I ("intima"), tunica media M ("media") which is the thickest layer of the wall, and the tunica adventitia A ("adventitia"). In some arteries an internal elastic membrane IEM is disposed between the media M and adventitia A. The adventitia A is made of collagen, vasa vasorum and nerve cells, the media M is made of smooth muscle cells, and the intima I is made up of a single layer of endothelial cells that provide a nonthrombogenic surface for flowing blood. An occlusion bypassing apparatus in accordance with embodiments hereof is used as part of a system for creating a subintimal reentry conduit within a wall of a blood vessel V to allow blood flow around an occlusion. FIGS. 13-23 illustrate an exemplary method of using the above-described occlusion bypassing apparatus 100 to bypass a chronic total occlusion (CTO) according to an embodiment hereof, but it would be understood by one of ordinary skill in the art that the depicted method may be adapted to be performed by other occlusion bypassing apparatus disclosed herein. Although described in relation to bypassing a CTO, it should be understood that the methods and apparatus described herein may be used for bypassing any tight stenoses in arteries or other anatomical conduits and are not limited to total occlusions.

Figure 13:
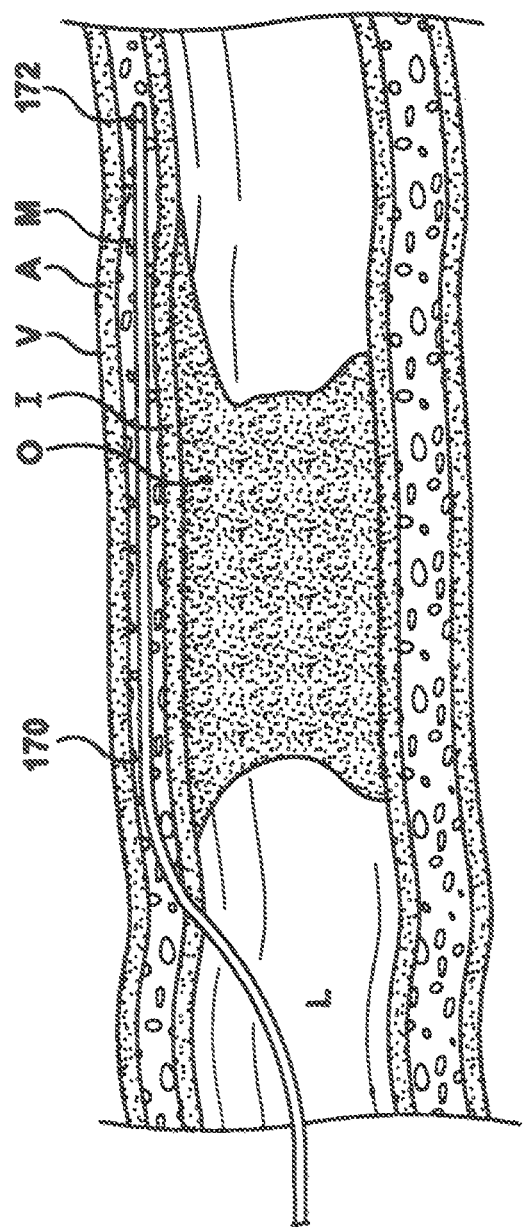

As shown in FIG. 13, in accordance with techniques known in the field of interventional cardiology and/or interventional radiology, a first guidewire 170 having a distal end 172 is transluminally advanced through the vasculature to a position upstream or proximal of a treatment site, which in this instance is shown as occlusion O within a lumen L of blood vessel V. Guidewire 170 pierces the intima I and is advanced distally to create a subintimal tract by locally dissecting or delaminating intima I from media M or by burrowing through media M. Guidewire 170 has a relatively larger outer diameter such as between 0.032-0.040 inches in order to have sufficient column strength to gain access to the subintimal space of vessel V. In order to pierce the intima I, a clinician may manipulate distal end 172 of guidewire 170 by prolapsing or bending-over the distal end of guidewire 170 (not shown) and thereafter may use the stiffer arc or loop of the prolapsed distal end to pierce into the intima I to advance guidewire 170 there through. The piercing of the intima I is aided by the fact that typically blood vessel V is diseased, which in some instances makes the intima I prone to piercing. Guidewire 170 is distally advanced within the subintimal tract from a near or proximal side of occlusion O to a position where distal end 172 thereof is positioned in the subintimal tract on a far or distal side of occlusion O.

Alternatively, another device other than guidewire 170 may be initially used to create the subintimal tract. Those of ordinary skill in the art will appreciate and understand the types of alternative devices that may be used in this step including an apparatus known as an "olive", a laser wire, an elongate radiofrequency electrode, or any other device suitable for boring or advancing through the vessel tissue. If an alternative device is used instead of guidewire 170 to form the subintimal tract, such alternative device may be removed and replaced with guidewire 170 or a smaller diameter guidewire after the subintimal tract has been formed.

After the subintimal tract is formed, outer shaft component 102 of occlusion bypassing apparatus 100 is tracked over guidewire 170 and advanced until distal end 106 of outer shaft component 102 is disposed at the far end of occlusion O as shown in FIG. 14. Once outer shaft component 102 is positioned as desired, balloon 112 may be inflated as shown in FIG. 15, thus anchoring outer shaft component 102 and in turn occlusion bypassing apparatus 100 in the subintimal tract. Guidewire 170 may then be proximally retracted and removed, and inner shaft component 114 with needle component 130 disposed therein are concurrently loaded into and advanced through outer shaft component 102 as shown in FIG. 16. During advancement or loading of the subassembly of inner shaft component 114 and needle component 130 through outer shaft component 102, angled distal tip segment 142 of needle component 130 is restrained or held in a straightened form within reinforced intermediate portion 128 of inner shaft component 114 as described above. In the alternate embodiment described above in which inner shaft component 114 does not include reinforced intermediate portion 128, the subassembly of the inner shaft component 114 and needle component 130 may still be concurrently loaded into and advanced through an indwelling or previously placed outer shaft component 102 with the combination of the inner and outer shaft components providing sufficient rigidity to maintain angled distal tip segment 142 of needle component 130 in a straightened form during loading and advancement of the subassembly.

Inner shaft component 114 and needle component 130 are advanced within outer shaft component 102 until flexible distal portion 124 of inner shaft component 114 distally extends from distal end 106 of outer shaft component 102, as shown in FIG. 16. Although inflation of balloon 112 is described as occurring prior to insertion of inner shaft component 114 and needle component 130, in another embodiment hereof (not shown) inflation of balloon 112 may not occur until after positioning of the inner shaft and needle components within outer shaft component 102 so long as balloon inflation occurs prior to bending and/or rotation of distal portion 124 of inner shaft component 114 as described herein.

After occlusion bypassing apparatus 100 is positioned adjacent to the far or downstream end of occlusion O as desired with balloon 112 inflated and flexible distal portion 124 of inner shaft component 114 distally extending from distal end 106 of outer shaft component 102, needle component 130 is distally advanced relative to inner shaft component 114 in order to bend flexible distal portion 124 of inner shaft component 114. More particularly, needle component 130 is distally advanced relative to inner shaft component 114 until angled distal tip segment 142 is disposed within flexible distal portion 124 that extends from distal end 106 of outer shaft component 102 to thereby bend flexible distal portion 124 away from the longitudinal axis of occlusion bypassing apparatus 100. When released from intermediate portion 128, needle component angled distal tip segment 142 resumes its shape memory bent or curved form and concurrently bends flexible distal portion 124 of inner shaft component 114 away from longitudinal axis $L_A$ of occlusion bypassing apparatus 100 to orient distal opening 126 of inner shaft component 114 towards true lumen L of vessel V. The position of distal portion 124 of inner shaft component 114 during bending thereof may be monitored via marker 110 thereon. If distal opening 126 of inner shaft component 114 is not oriented or pointed towards true lumen L of vessel V, a proximal end 132 of needle component 130 may be rotated or turned by a physician. When needle component 130 is rotated, inner shaft component 130 with its flexible distal portion 124 in its bent or deployed configuration rotates therewith as described above and as shown by a directional arrow 174 in FIG. 17 to make any necessary adjustment of the rotational position or orientation of inner shaft component 114 and needle component 130 within the subintimal tract to ensure that distal tip 136 of needle component 130 will be deployed into a specific radial location, i.e. into the intima I, on the vessel wall. The correct rotational position or orientation of inner shaft component 114 and needle component 130 is shown in FIG. 18, with distal opening 126 of inner shaft component 114 oriented toward the true lumen of the vessel. During bending of distal portion 124 of inner shaft component 114 and any rotation of the inner shaft component and needle component 130, needle component distal tip 136 is disposed within inner shaft component 114.

Once distal opening 126 of inner shaft component 114 is oriented towards the vessel true lumen as desired, needle component 130 is distally advanced relative to inner shaft component 114 until distal tip 136 extends from or protrudes out of distal opening 126 of inner shaft component 114 and penetrates the intima to gain access to the true lumen of the vessel distal to, i.e., downstream of, the CTO as shown in FIG. 19. Angled distal tip segment 142 of needle component 130 still extends through and bends flexible distal portion 124 of inner shaft component 114 away from longitudinal axis $L_A$ of occlusion bypassing apparatus 100.

Figure 21:
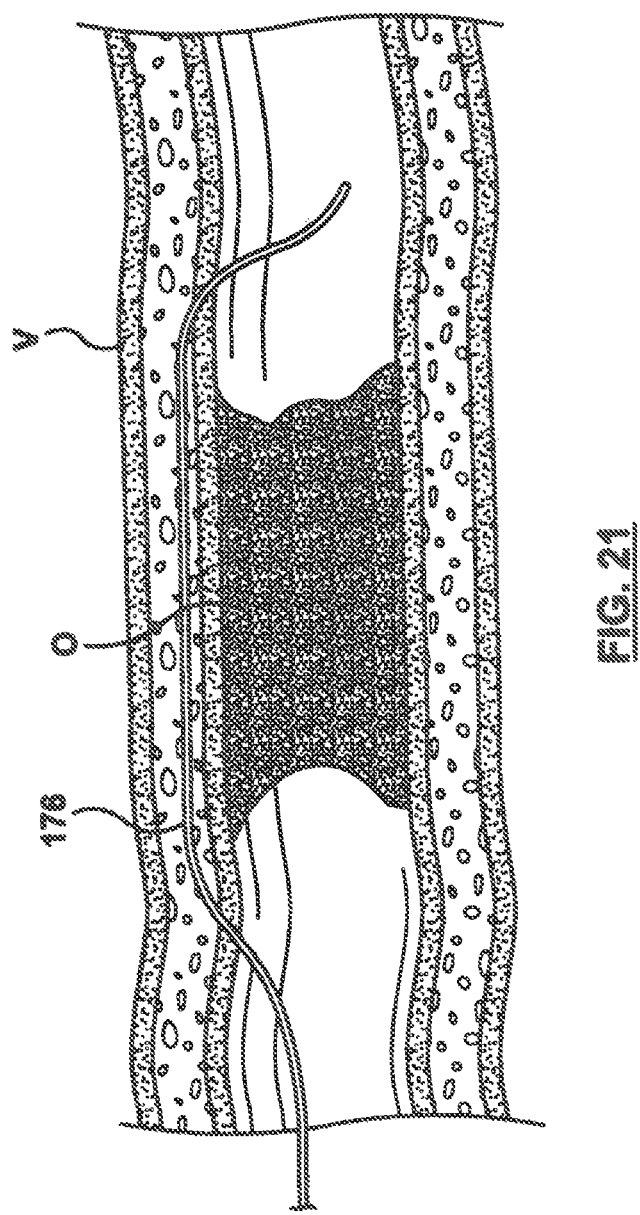

A second guidewire 176 may be advanced through lumen 138 of needle component 130 and into the true lumen L of vessel V as shown in FIG. 20. Guidewire 176 has a relatively smaller outer diameter such as 0.014 inches in order to minimize the size of needle component 130 and subsequently minimize the size of occlusion bypassing apparatus 100. Optionally, occlusion bypassing apparatus 100 may be removed and guidewire 176 may be left in place as shown in FIG. 21, such that guidewire 176 extends in true lumen L proximal to the CTO, through the subintimal tract, and back into true lumen L distal to the CTO to enable the CTO to be successfully crossed via the subintimal conduit thus created.

Figure 22:
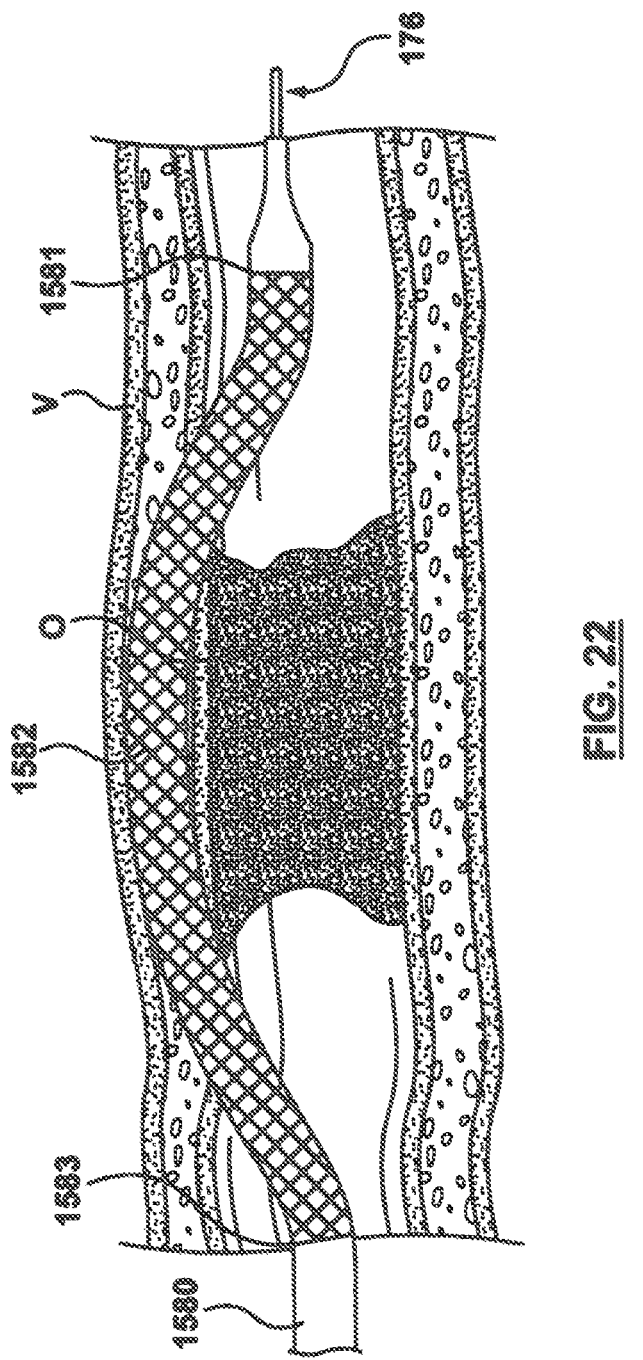
Figure 23:
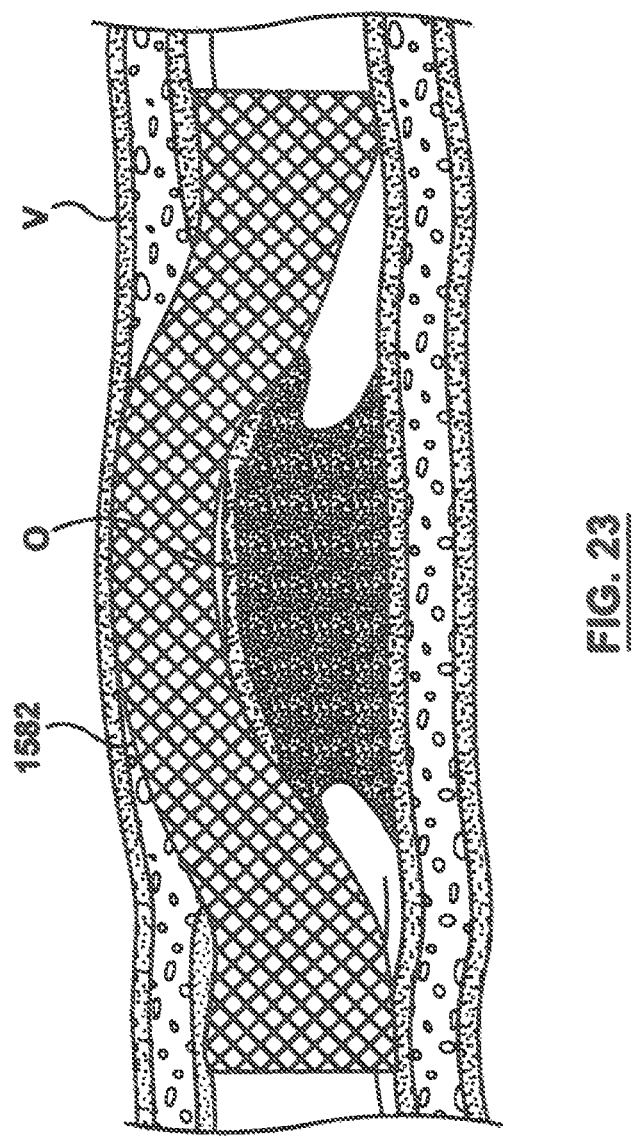

Optionally, a covered or uncovered stent may be delivered over guidewire 176 and implanted within the subintimal tract to facilitate flow from the lumen of the vessel upstream of the CTO, through the subintimal tract and back into the lumen of the vessel downstream of the CTO. For example, FIG. 22 shows a distal end of a catheter 1580 having a stent 1582 mounted thereon being advanced over guidewire 176 to a position where a distal end 1581 of the radially collapsed stent 1582 is in true lumen L of vessel V downstream of chronic total occlusion CTO, a proximal end 1583 of stent 1582 is in true lumen L of vessel V upstream of chronic total occlusion CTO, and a tubular body of stent 1582 extends through the subintimal tract. Stent 1582 is then deployed by either self-expansion or balloon inflation within the subintimal reentry conduit to dilate the subintimal tract and compress the adjacent chronic total occlusion CTO. Stent 1582 provides a scaffold which maintains the subintimal tract in an open condition capable of carrying blood downstream of chronic total occlusion CTO. Thereafter, guidewire 176 and catheter 1580 may be removed from the patient, leaving stent 1582 in an expanded configuration and creating a radially supported, subintimal blood flow channel around chronic total occlusion CTO as seen in FIG. 23. In some cases, it may be desirable to enlarge the diameter of the subintimal tract before advancing stent catheter 1580 into and through it. Such enlargement of the subintimal tract may be accomplished by passing a balloon dilatation catheter over guidewire 176 and inflating the balloon to dilate the tract, or may be any other suitable tract enlarging, dilating or de-bulking instrument that may be passed over guidewire 176.

Figure 24:
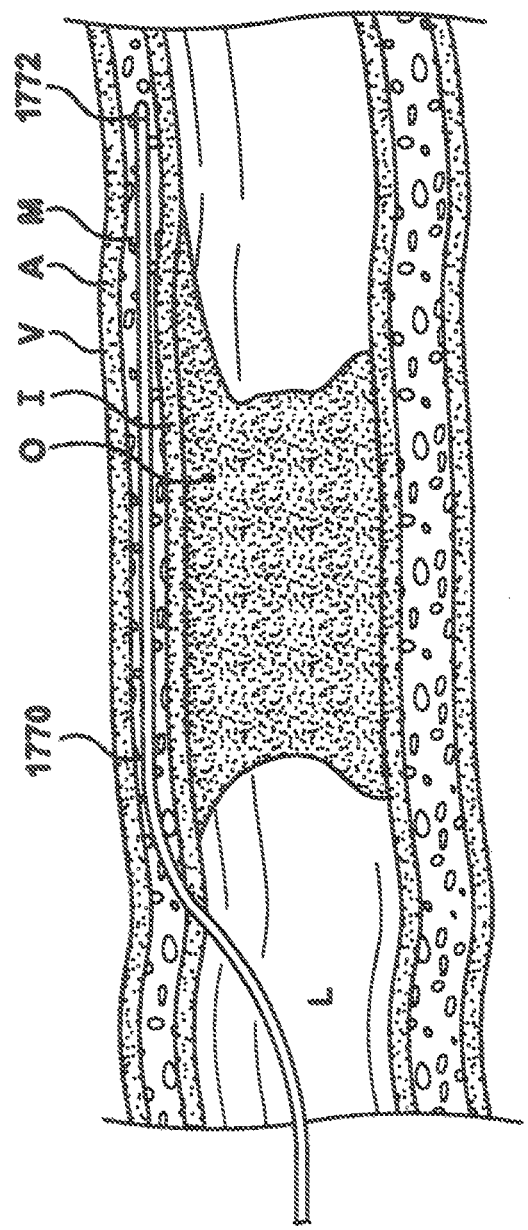
Figure 25:
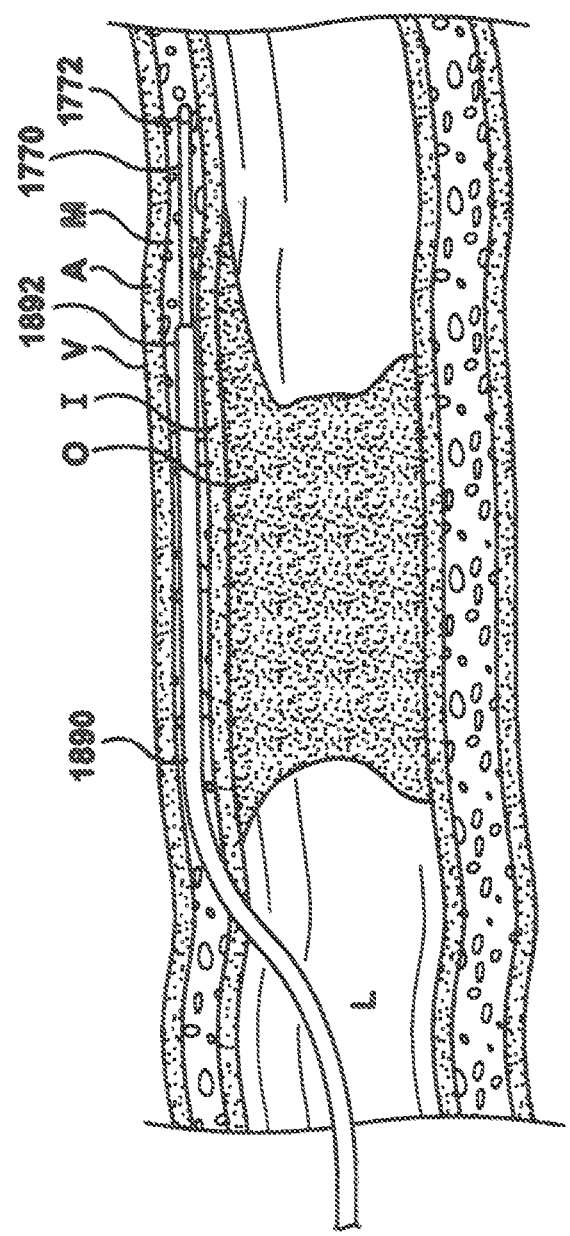
Figure 26:
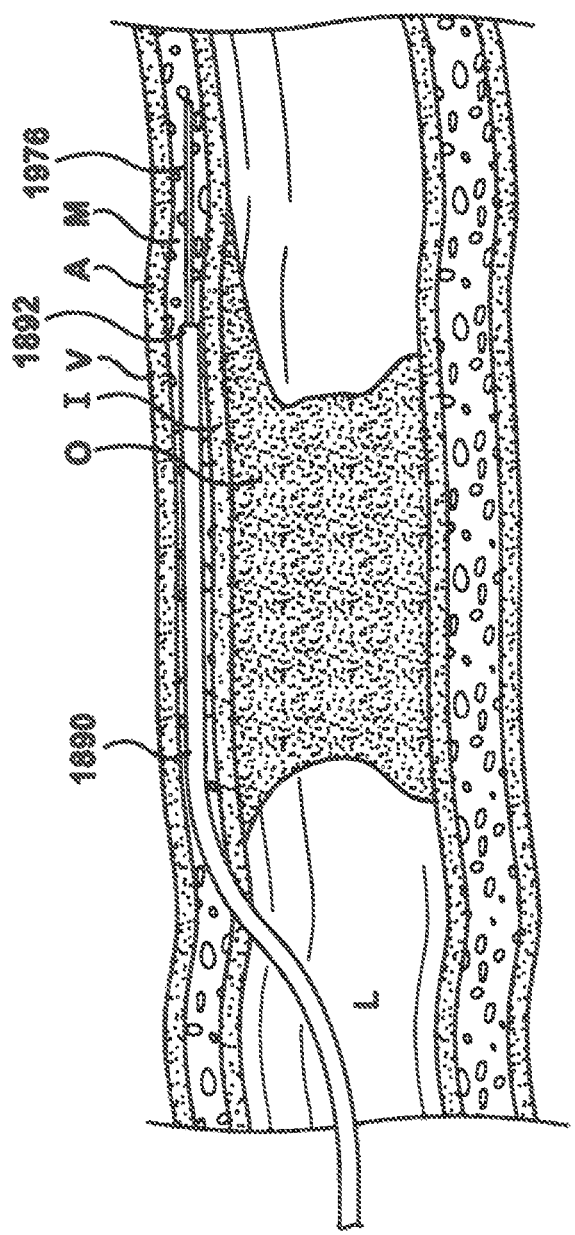

FIGS. 24-29 illustrate an alternative method of forming a subintimal tract and positioning occlusion bypassing apparatus 100 adjacent to the distal or downstream end of occlusion O, but it would be understood by one of ordinary skill in the art that the depicted method may be adapted to be performed by other occlusion bypassing apparatus disclosed herein. With reference to FIG. 24, a first guidewire 1770 having a distal end 1772 is transluminally advanced through the vasculature to a position proximal or upstream of a total occlusion O within a lumen L of blood vessel V. Similar to guidewire 170, guidewire 1770 has a relatively larger outer diameter in order to have sufficient column strength to gain access to the subintimal space of vessel V and guidewire 1770 is utilized to pierce the intima I and create a subintimal tract between the intima I and the media M. A guide catheter 1890 is then tracked over guidewire 1770 and advanced such that a distal end 1892 thereof is adjacent to the distal or downstream end of occlusion O as shown in FIG. 25. Guidewire 1770 may then be proximally retracted and removed, and a relatively smaller second guidewire 1976 may be loaded into and advanced through guide catheter 1890 as shown in FIG. 26. In an embodiment, second guidewire 1976 has a relatively smaller outer diameter such as 0.014 inches.

Figure 27:
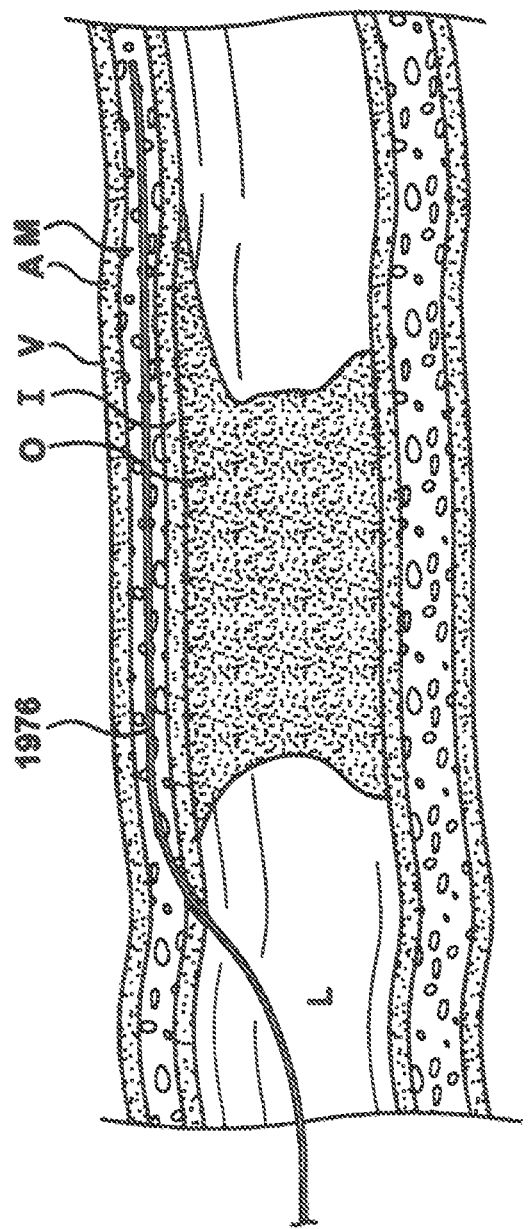
Figure 28:
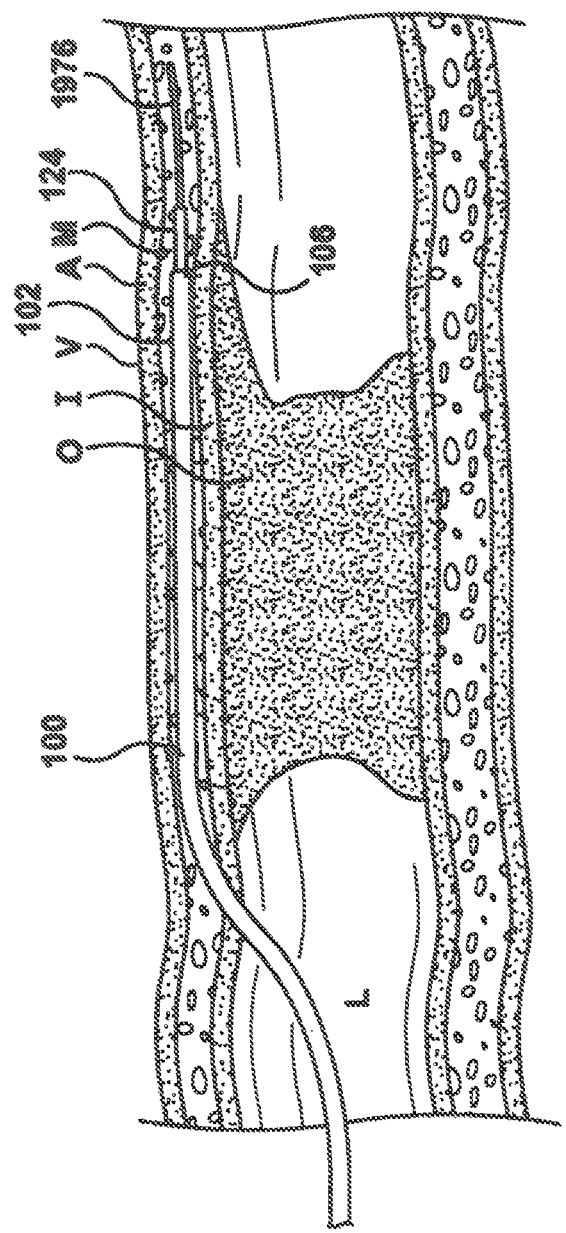
Figure 29:
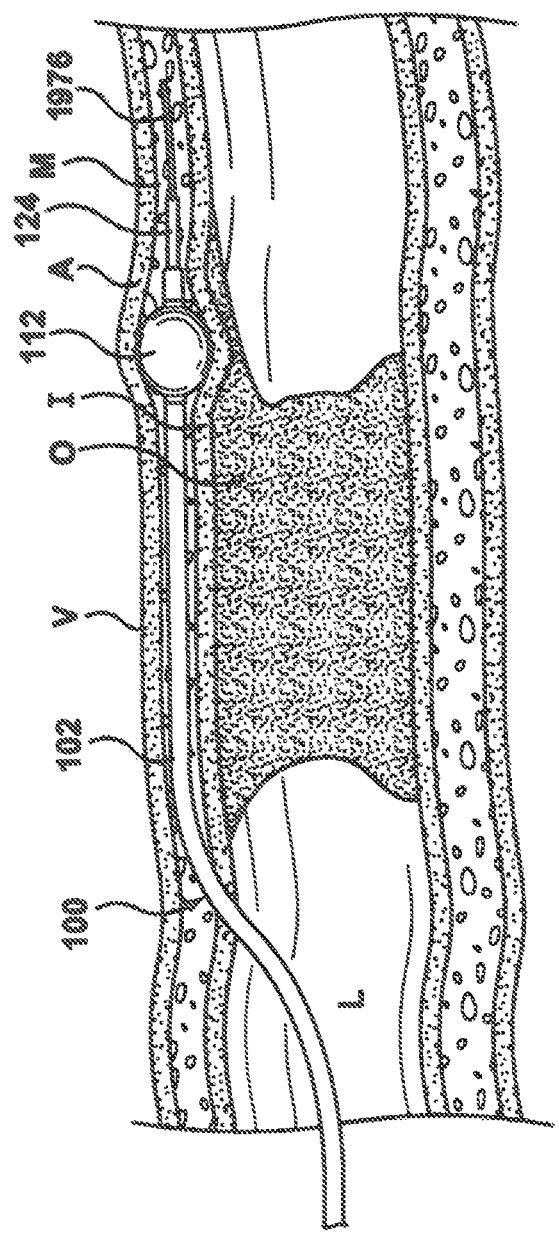

After second guidewire 1976 is in place as desired, guide catheter 1890 may be proximally retracted and removed as shown in FIG. 27, leaving only second guidewire 1976 extending into the subintimal tract. At this point, occlusion bypassing apparatus 100 may be tracked over second guidewire 1976 and advanced such that a distal end 106 is adjacent to the distal end of occlusion O as shown in FIG. 28. In this embodiment, outer shaft component 102, inner shaft component 114, and needle component 130 are concurrently advanced as an ensemble over second guidewire 1976 rather than advancing the outer shaft component prior to the inner shaft and needle components as described in the prior embodiment. Stated another way, inner shaft component 114 and needle component 130 are loaded into outer shaft component prior to the step of advancing occlusion bypassing apparatus 100 over guidewire 1976. As shown in FIG. 28, during distal advancement of occlusion bypassing apparatus 100, flexible distal portion 124 of inner shaft component 114 may distally extend from distal end 106 of outer shaft component 102 as long as angled distal tip segment 142 of needle component 130 is restrained or held in a straightened form within inner shaft component intermediate portion 128, if applicable, or by the interaction of outer and inner shaft components 102, 114 in embodiments in which the intermediate portion is not present. Once occlusion bypassing apparatus 100 is positioned as desired, balloon 112 may be inflated as shown in FIG. 29 to anchor outer shaft component 102 in the subintimal tract. Guidewire 1976 may be proximally retracted and removed, leaving only occlusion bypassing apparatus 100 extending through the subintimal tract. Similarly in the alternate embodiment described above in which inner shaft component 114 does not include intermediate portion 128, the whole ensemble of the outer shaft component 102, inner shaft component 114, and needle component 130 may be concurrently advanced over the already in place guidewire 1976 and tracked to the lesion where balloon 112 is then expanded.

Once occlusion bypassing apparatus 100 is positioned adjacent to the distal end of occlusion O as desired with balloon 112 inflated, the remaining steps to create a subintimal conduit that bypasses the occlusion O are the same as described with respect to FIGS. 17-23. More particularly, distal portion 124 of inner shaft component may be bent via advancement of needle component 130 and the needle and inner shaft components may be rotated as described above with respect to FIGS. 17-18. Distal tip 136 of needle component 130 is then distally advanced to penetrate through the intima and thereafter pass into the true lumen of the vessel as described with respect to FIG. 19, and a guidewire may be advanced through needle component 130 into the true lumen of the vessel as described with respect to FIG. 20. Optionally, a stent may be delivered and implanted within the subintimal tract to facilitate flow from the lumen of the vessel proximal of the CTO, through the subintimal tract and back into the lumen of the vessel distal of the CTO as described with respect to FIGS. 21-23.

In a method of forming a subintimal tract and positioning occlusion bypassing apparatus 500 adjacent to the downstream end of an occlusion, a balloon catheter of occlusion bypassing apparatus 500 comprising shaft component 502 and balloon 512 is tracked over an indwelling guidewire, such as guidewire 170 shown in FIG. 13, through the subintimal tract until distal tip 525 of the catheter is disposed at the distal side of the occlusion. Balloon 512 is then inflated to anchor the balloon catheter within the subintimal tract, as similarly shown in the embodiment of FIG. 15. Needle component 530 that is held in a straightened configuration by stylet 531 is then advanced relative to the balloon catheter until distal tip segment 642 of the needle component extends within distal shaft portion 524 of the balloon catheter. The distal tip segment 642 of needle component 530 is then gradually and under control returned to its shape memory angled configuration in which it bends away from a longitudinal axis of proximal portion 640 of the needle component 530 by distal advancement of needle component 530 relative to stylet 531 and distal shaft portion 524. Stylet 531 is then removed from needle component 530 and distal tip 636 of needle component 530, which extends from distal tip 525 of shaft component 502, is then distally advanced and positioned to penetrate through the intima and thereafter pass into the true lumen of the vessel. The remainder of the method of forming the subintimal tract may proceed as described above with reference to FIGS. 20-23.

In a method of forming a subintimal tract and positioning occlusion bypassing apparatus 900 adjacent to the downstream end of an occlusion, occlusion bypassing apparatus 900 comprising shaft component 902, balloon 912 and needle component 530 is advanced over an indwelling guidewire, such as guidewire 170 shown in FIG. 13, through the subintimal tract until distal tip 925 of the apparatus is disposed at the distal side of the occlusion. Balloon 912 is then inflated to anchor the apparatus within the subintimal tract, as similarly shown in the embodiment of FIG. 15. Needle component 530 is held in a straightened form by metallic shaft segment 928 of shaft component 902 during the advancement of occlusion bypassing apparatus 900 to the treatment site. Needle component 530 is then advanced relative to shaft component 902 until at least a portion of angled distal tip segment 642 is disposed within distal portion 924 of shaft component 902 to thereby bend distal portion 924 away from a longitudinal axis of the occlusion bypassing apparatus. The distal tip segment 642 of needle component 530 is then positioned such that subsequent distal advancement relative to shaft component 902 will cause the distal tip 636 to penetrate through the intima and thereafter pass into the true lumen of the vessel. The remainder of the method of forming the subintimal tract may proceed as described above with reference to FIGS. 20-23.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, although inner shaft component 114 is primarily described to include a relatively stiff intermediate portion 128 for holding angled distal tip segment 142 of needle component 130 in a straightened position during loading and/or advancement, in another embodiment, as discussed in various places above, the combination or subassembly of outer shaft component 102 and proximal portion 122 of inner shaft component 114 has a sufficient stiffness to hold the angled distal tip segment of needle component in a straightened position during loading and/or advancement. As such, angled distal tip segment 142 of needle component 130 is restrained in a straightened position when disposed within both outer shaft component 102 and inner shaft component 114 but resumes its bent shape when disposed only within flexible distal portion 124 of inner shaft component 114. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. An apparatus for bypassing an occlusion in a blood vessel comprising:
   a shaft component defining a lumen that extends from a proximal end to distal end thereof and having a distal tip portion that is bendable relative to a proximal portion thereof, the shaft component having at least one balloon secured to extend from an outer surface of the shaft component proximate of the distal tip portion thereof such that the shaft component and the balloon comprise a portion of a balloon catheter; and
   a needle component configured to be slidably disposed within the shaft component lumen and removable therefrom, the needle component having a proximal segment and an angled distal tip segment, wherein in a first configuration of the apparatus the angled distal tip segment of the needle component is held in a straightened form within the shaft component and wherein in a second configuration of the apparatus the angled distal tip segment of the needle component bends the distal tip portion of the shaft component away from a longitudinal axis of the proximal portion.

2. The apparatus of claim 1, wherein in the second configuration the distal tip portion of the shaft component is at an acute angle with respect to the longitudinal axis of the proximal portion of the shaft component.

3. The apparatus of claim 1, wherein the proximal portion of the shaft component is a polymeric tube having a reinforcing layer.

4. The apparatus of claim 1, wherein the shaft component further includes a metallic shaft segment disposed between the proximal portion and the distal tip portion and wherein the angled distal tip segment of the needle component is held in the straightened form by the metallic shaft segment when the apparatus is in the first configuration.

5. The apparatus of claim 1, wherein the at least one balloon is more than one balloon mounted on opposing sides of the shaft component that stabilize the shaft component in an inflated configuration.

6. The apparatus of claim 5, wherein each of the balloons has an asymmetrical cross-section such that in the inflated configuration the balloons extend away from each other in opposite directions.

7. The apparatus of claim 1, further comprising:
   a radiopaque marker attached to the distal tip portion of the shaft component that is configured to permit an orientation of the distal tip portion to be visualized under fluoroscopy.

8. The apparatus of claim 1, wherein the shaft component is a hypotube having a spiral cut segment in the distal tip portion thereof.

9. The apparatus of claim 1, wherein the angled distal tip segment of the needle component has a tip for penetrating a wall of the vessel.

10. The apparatus of claim 1, wherein the angled distal tip segment of the needle component is held in the straightened form by an elongate stylet that extends therethrough.

11. An apparatus for bypassing an occlusion in a blood vessel comprising:
    an outer shaft component defining a lumen that extends from a proximal end to distal end thereof;
    an inner shaft component defining a lumen that extends from a proximal end to distal end thereof and having a distal tip portion that is bendable relative to a proximal portion thereof, wherein the inner shaft component is configured to be slidably and rotatably disposed within the outer shaft component lumen and removable therefrom;
    at least one balloon mounted on the outer shaft component proximate of the distal end thereof; and
    a needle component configured to be slidably disposed within the inner shaft component, the needle component having a proximal segment and an angled distal tip segment, wherein in a first configuration of the apparatus the angled distal tip segment of the needle component is held in a straightened form within the apparatus and wherein in a second configuration of the apparatus the angled distal tip segment of the needle component positions the distal tip portion of the inner tubular component at an acute angle with respect to a longitudinal axis of the apparatus, and wherein without the angled distal tip segment of the needle component slid therein, the bendable distal tip portion of the inner shaft component is straight and aligned with the proximal portion of the inner shaft component.

12. The apparatus of claim 11, wherein the angled distal tip segment of the needle component is held in the straightened form when disposed within both the inner and outer shaft components when the apparatus is in the first configuration.

13. The apparatus of claim 11, wherein the proximal portion of the inner shaft component is a polymeric tube having a reinforcing layer.

14. The apparatus of claim 11, wherein the inner tubular component further includes a metallic tubular segment disposed between the proximal portion and the distal tip portion and wherein the angled distal tip segment of the needle component is held in the straightened form by the metallic tubular segment when the apparatus is in the first configuration.

15. The apparatus of claim 11, wherein the at least one balloon is more than one balloon mounted on opposing sides of the outer shaft component that stabilize the outer shaft component in an inflated configuration.

16. The apparatus of claim 15, wherein each of the balloons has an asymmetrical cross-section such that in the inflated configuration the balloons extend away from each other in opposite directions.

17. The apparatus of claim 11 further comprising:
    a radiopaque marker attached to the distal tip portion of the inner shaft component that is configured to permit an orientation of the distal tip portion to be visualized under fluoroscopy.

18. The apparatus of claim 11, wherein the angled distal tip segment of the needle component has a tip for penetrating a wall of the vessel.

19. The apparatus of claim 11, wherein the angled distal tip segment of the needle component is held in the straightened form by an elongate stylet that extends therethrough.

20. The apparatus of claim 11, wherein the inner shaft component is a hypotube having a spiral cut segment in the distal tip portion thereof.

* * * * *